United States Patent

Lippitt et al.

[11] Patent Number: 5,906,622
[45] Date of Patent: May 25, 1999

[54] POSITIVELY EXPANDED AND RETRACTED MEDICAL EXTRACTOR

[76] Inventors: Robert G. Lippitt, 515 Rosewood Dr., Smithfield, N.C. 27577; Raymond F. Lippitt, 8601 Burning Tree Rd., Bethesda, Md. 20817

[21] Appl. No.: 09/069,159

[22] Filed: Apr. 29, 1998

Related U.S. Application Data

[60] Provisional application No. 60/045,068, Apr. 29, 1997, provisional application No. 60/056,507, Aug. 21, 1997, provisional application No. 60/045,322, May 1, 1997, and provisional application No. 60/056,533, Aug. 21, 1997.

[51] Int. Cl.$^6$ .................................................. A61B 17/22
[52] U.S. Cl. ........................... 606/127; 606/128; 606/113
[58] Field of Search .................................. 606/127, 128, 606/106, 25, 110, 113; 604/264, 265

[56] References Cited

U.S. PATENT DOCUMENTS

| 4,471,777 | 9/1984 | McCorkle, Jr. . | |
| 5,387,291 | 2/1995 | Rappe | 606/113 |
| 5,522,819 | 6/1996 | Graves et al. | 606/113 |
| 5,613,973 | 3/1997 | Jackson et al. | 606/113 |

FOREIGN PATENT DOCUMENTS

| 0 769 305 | 4/1997 | European Pat. Off. . |
| 29 45 237 | 5/1981 | Germany . |
| 37 17 657 | 12/1988 | Germany . |
| WO 94 06357 | 3/1994 | WIPO . |

*Primary Examiner*—Michael Buiz
*Assistant Examiner*—Lien Ngo

[57] ABSTRACT

A medical extractor comprising a cannula assembly having an annularly expanding and retracting gripping and releasing mechanism on the distal end thereof and a moving assembly on the proximal end thereof. The arrangement is such that a manual movement of the moving assembly in one direction effects a longitudinally outward movement of an annular array of longitudinally movable wire flexure elements within an annular array of longitudinally fixed tubular flexure elements to cause the fixed flexure elements to flex transversely outwardly and create an annularly expanded condition defined by an annular series of transversely outwardly flexed fixed flexure elements interconnected at their ends by an annular series of arcuately outwardly flexed portions of the movable flexure elements. A manual movement in the opposite direction effects a longitudinally inward movement of the movable flexure elements to cause the expanded condition to progressively retract during which the outwardly flexed fixed flexure elements are progressively less flexed transversely outwardly and the arcuately flexed portions of the movable flexure elements have a progressively less arcuate extent.

32 Claims, 8 Drawing Sheets

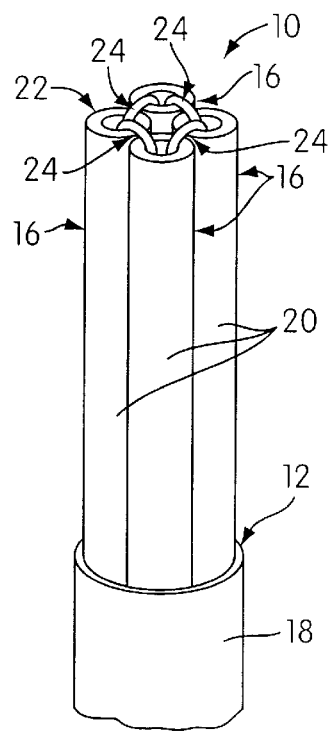
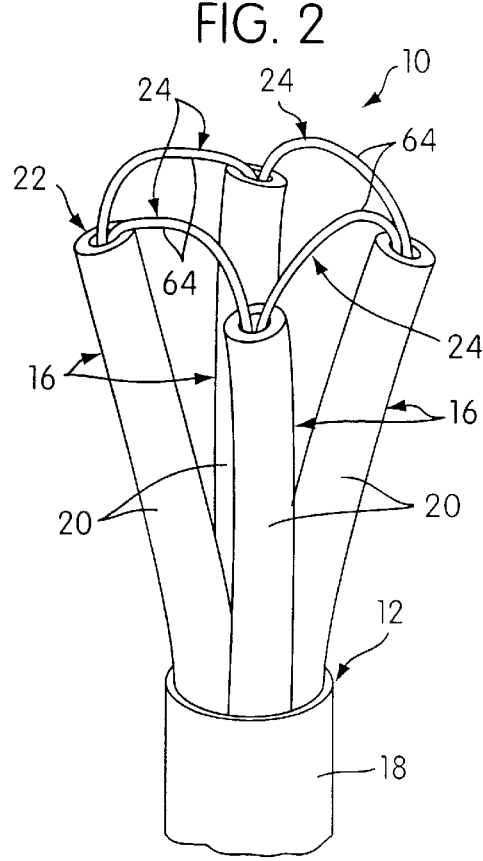
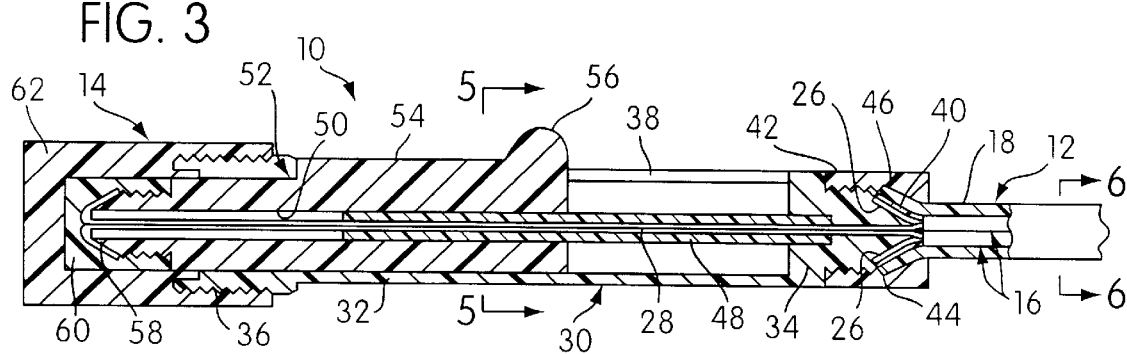
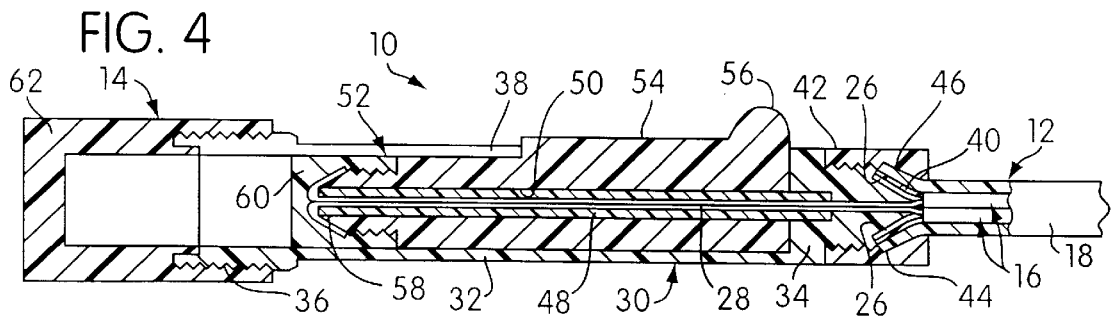

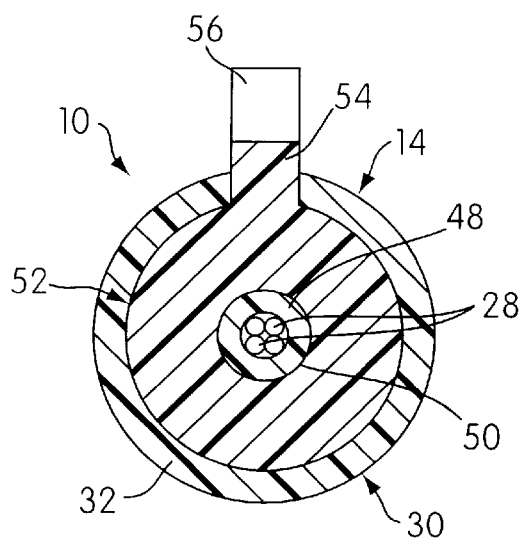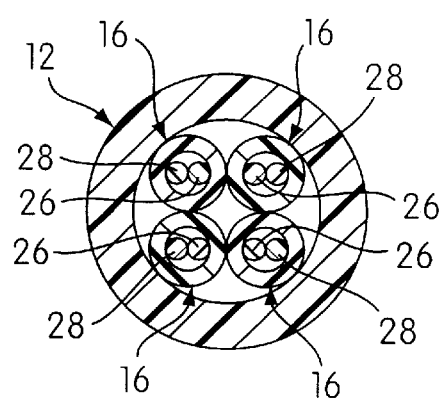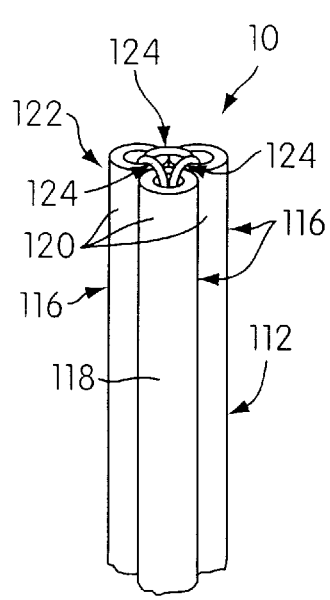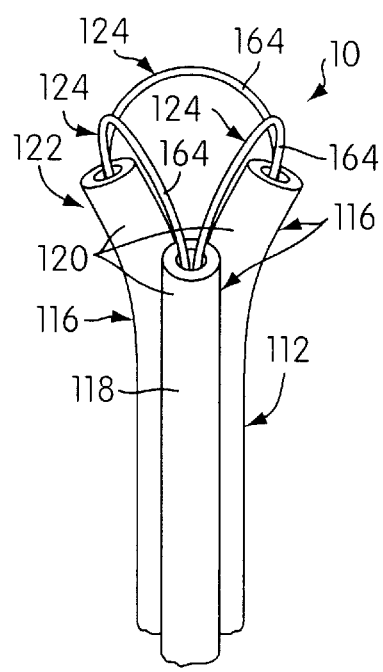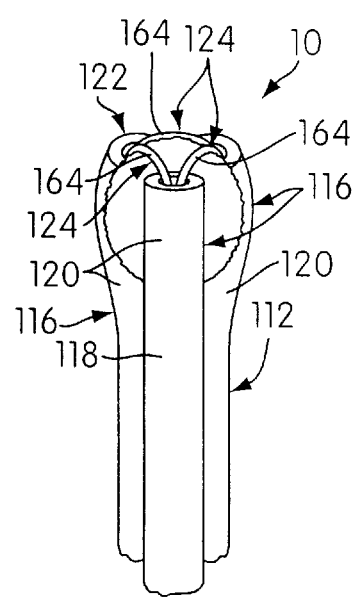

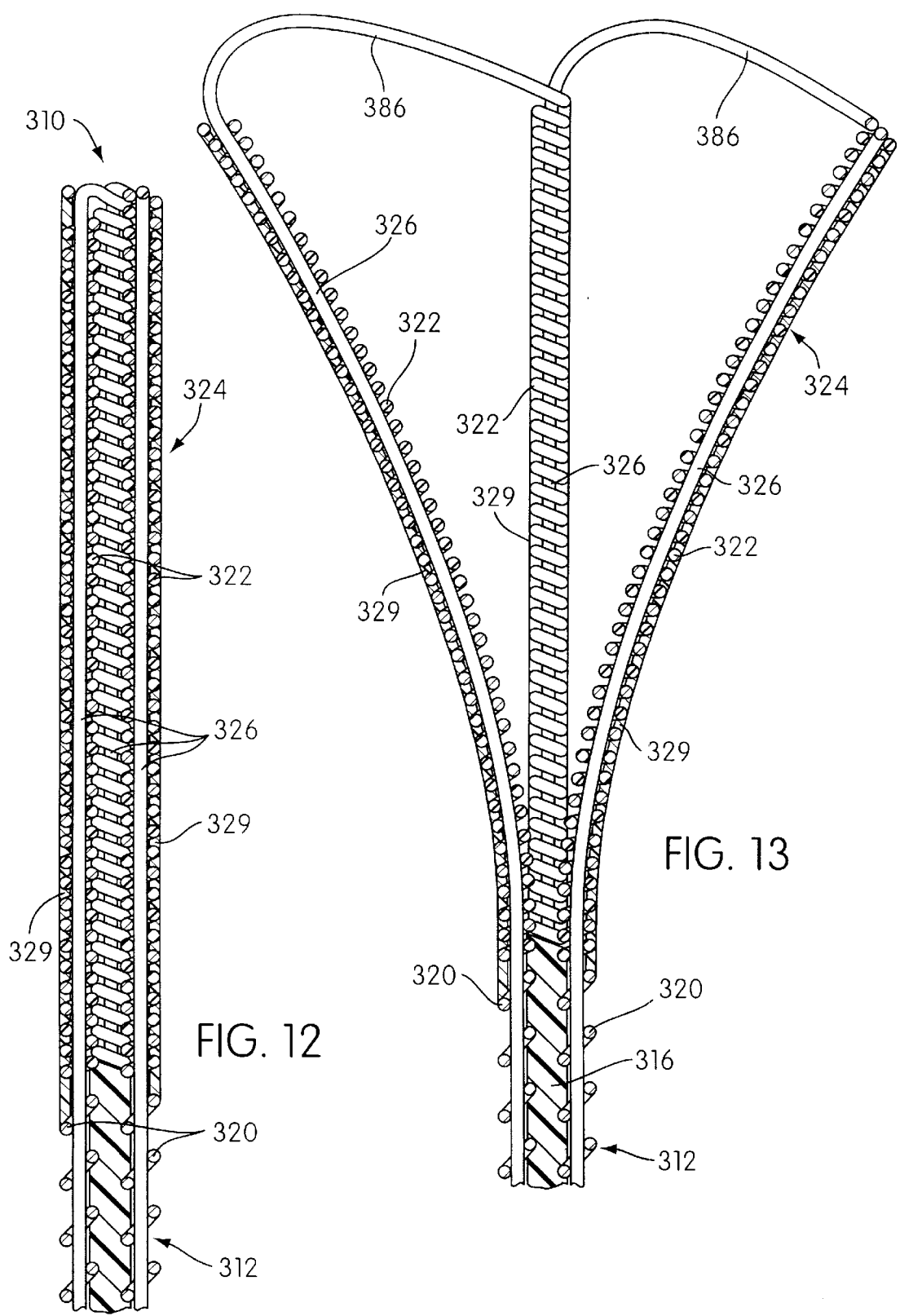

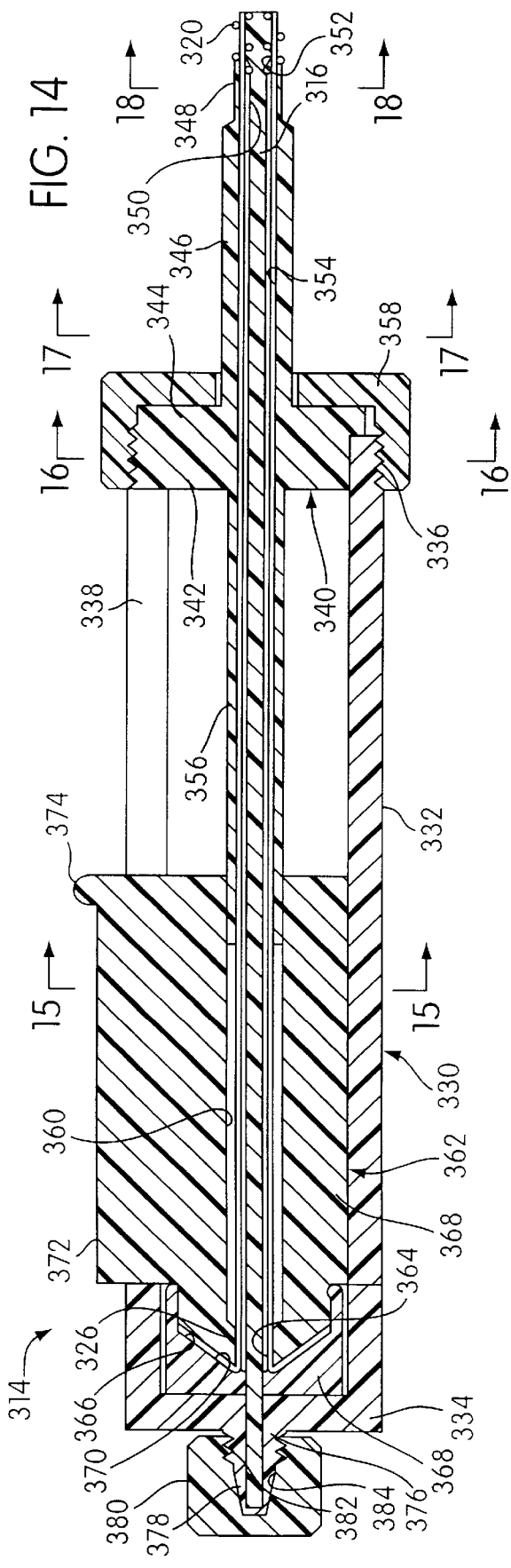
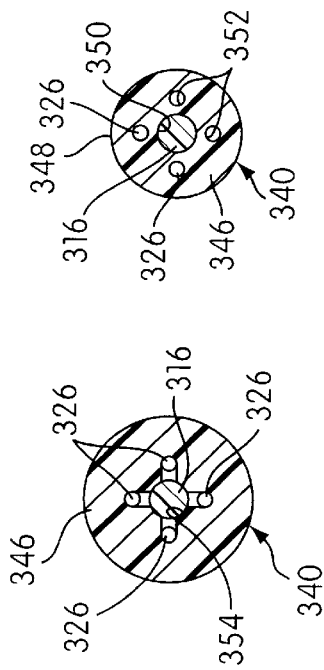
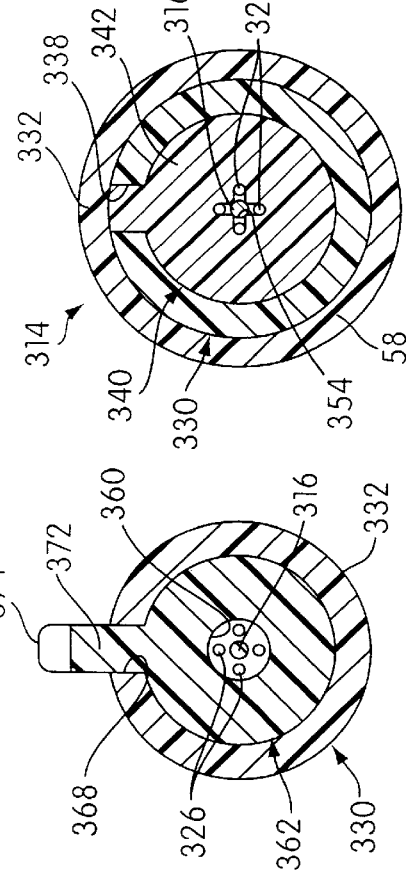

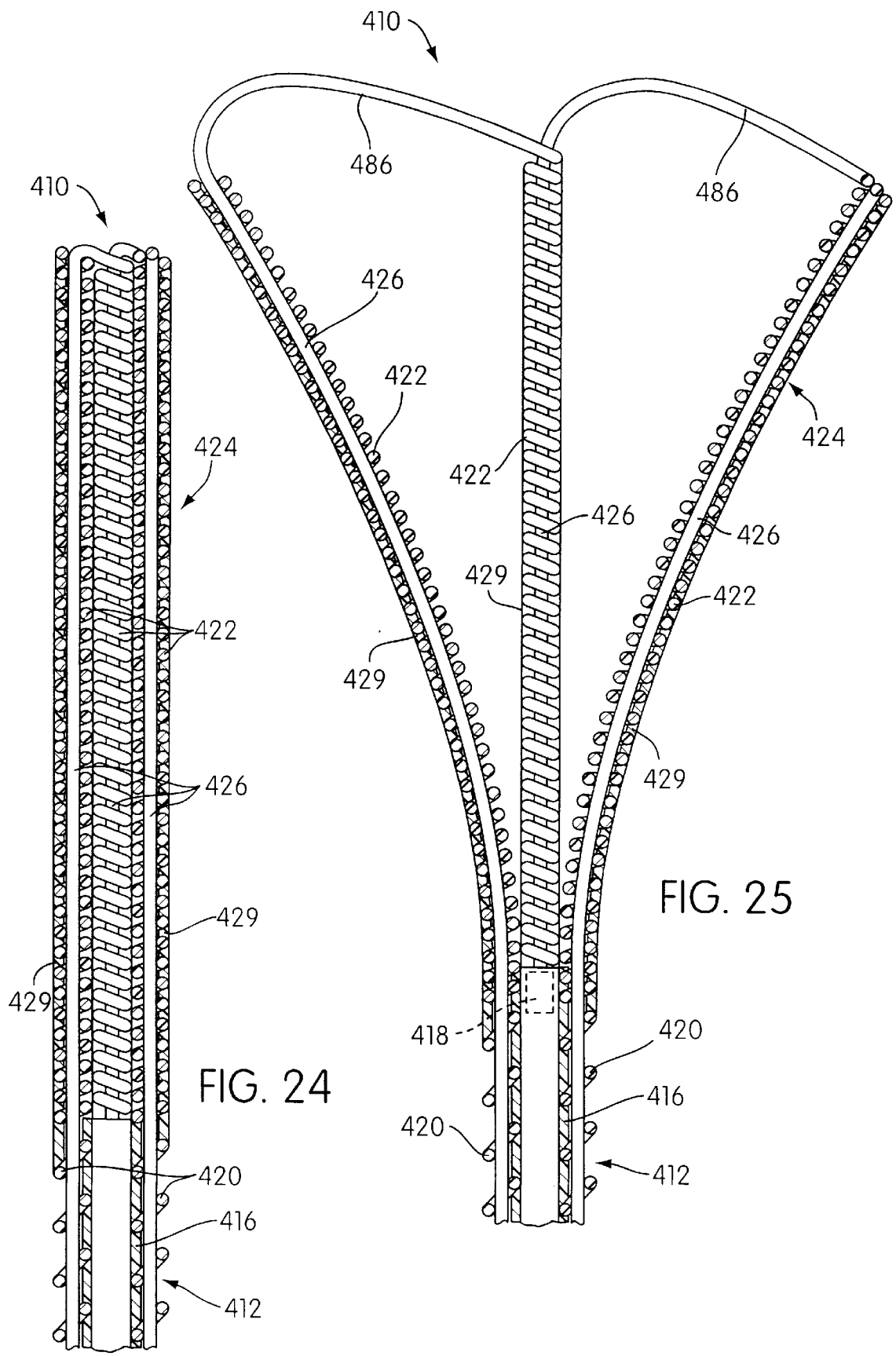

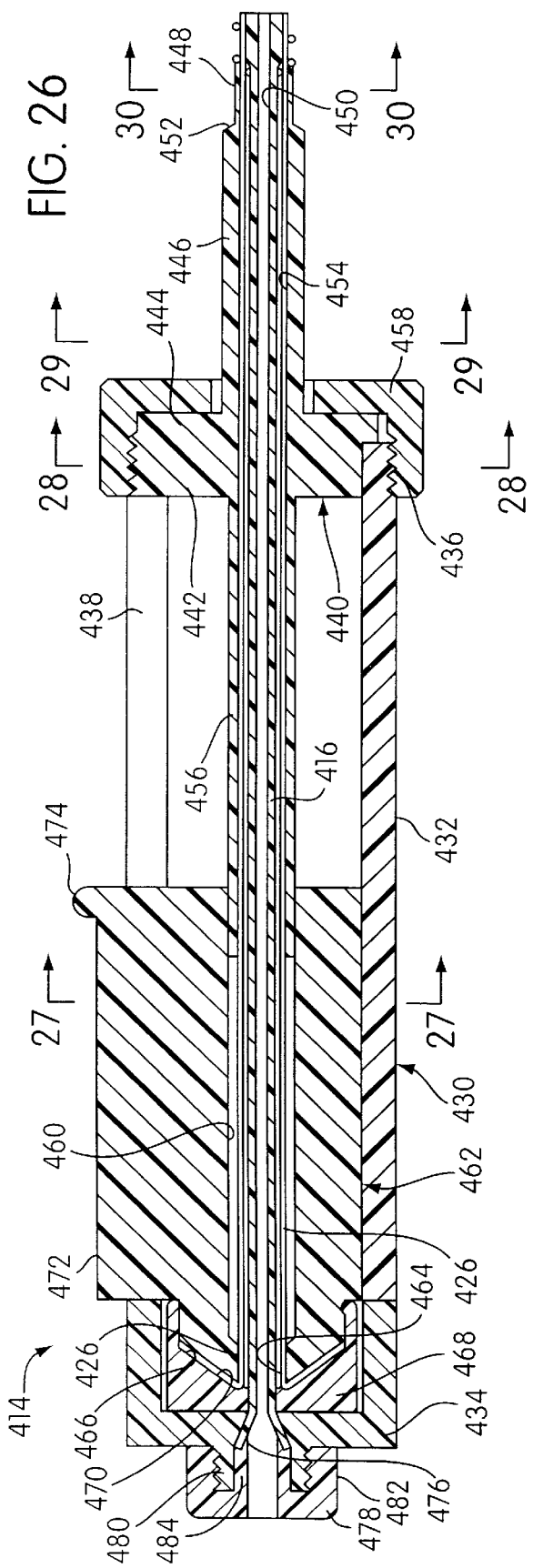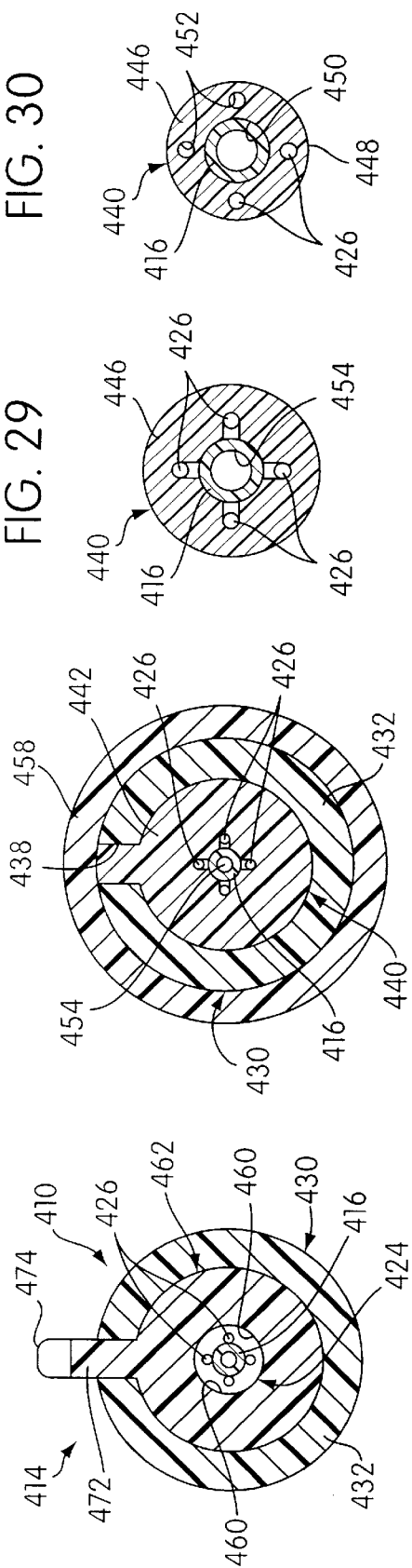

5,906,622

POSITIVELY EXPANDED AND RETRACTED MEDICAL EXTRACTOR

This application claims the benefit of U.S. provisional application Ser. No. 60/045,068, filed Apr. 29, 1997, U.S. provisional application Ser. No. 60/045,322, filed May 1, 1997; U.S. provisional application Ser. No. 60/056,507, filed Aug. 21, 1997, and U.S. provisional application Ser. No. 60/056,533, filed Aug. 21, 1997.

This invention relates to medical extractors and more particularly to extractors especially constructed to extract kidney stones from the kidney of a patient.

The treatment of urolithiasis has changed dramatically since the implementation of Extracorporeal Shockwave Lithotripsy (ESL). The procedure fragments stones in a non-invasive manner into small particles that can more easily pass. While ESL will continue to be the primary treatment modality of urolithiasis, there are subsets of patients who require alternative methods.

Small stones in the distal ureter can be more reliably and definitively extracted with ureteroscopic stone basketing. Radiolucent stones can be directly visualized with pyeloureteroscopes and lithotriped either with electrohydrolic or laser techniques and/or basketed. If the stones are not visualized radiographically during ESL, the ESL energy cannot be directed upon them. Very large stone volumes have significant problems passing after ESL and percutaneous nephrostolithotomy is recommended as primary treatment or in combination with ESL for these stones. Minimally invasive techniques can effectively treat anatomical abnormalities that can predispose to stone development as well as treat the urolithiasis. ESL has a limited effective focal area and a limit to how much energy that can be applied to the kidney in one treatment. If a patient has multiple stones in one kidney distributed in the upper, middle and lower poles, multiple ESL treatments would be necessary versus one minimally invasive treatment. Some stones, such as calcium oxalate monohydrate, brushite, cystine stones are so hard that ESL has difficulty cracking them or getting the fragment size small enough to easily spontaneously pass. Certain patients require stone-free status, such as pilots, and minimally invasive stone extraction can be more definitive than ESL. Also, stone-free status is especially important in patients with infected stones where the stone harbors bacteria. The minimally invasive approach has significant applications that are likely to persist as the limitations of ESL are apparent.

During the last ten years, there has been continued improvement and miniaturization of the instruments used in the minimally invasive treatments of urolithiasis. There exist excellent methods of fragmenting stones through small stearable pyeloureteroscopes. Presently, wide range of ureteroscopic baskets are commercially available. These all consist of wires slidably mounted in a tubular sleeve forming the canula. The distal ends of the wires are secured together to form an end plug and the adjacent portions of the wires are capable of expanding when extended outwardly by virtue of the resiliency of the metal used. If the containing sleeve which when retracted serves to retract the extended wires. In the tube like ureter, the end plug is acceptable but, in the blunt rounded renal calyces, it presents problems. The end plug creates distance from the end to the functional engaging portion of the basket making stone entrapment difficult. Also, the end plug tends to pierce the renal calyceal urothelial lining causing bleeding which obscures visualization and possibly leads to the termination of the procedure.

The existing alternative to this type of basket is an end alligator-like or bent wire-grasping instrument which inadequately entraps stones for extraction. There exists a need to provide an extractor which will overcome the problems noted above.

It is an object of the present invention to fulfill the need enunciated above. In accordance with the principles of the present invention, this objective is achieved by providing a medical extractor comprising an elongated cannula assembly having a distal end constructed and arranged to be inserted into a patient and a proximal end constructed and arranged to be retained exteriorly of the patient. The cannula assembly has an annularly expanding and retracting gripping and releasing mechanism at the distal end thereof and a manually movable moving assembly at the proximal end thereof. The annularly expanding and retracting mechanism includes an annular series of longitudinally fixed flexure elements and a corresponding series of longitudinally movable flexure elements. The fixed flexure elements are fixed relatively together in an annular array at a confining fixed position and have a flexure position spaced longitudinally outwardly therefrom. Each of the fixed flexure elements is constructed and arranged to flex at the flexure position thereof transversely outwardly and inwardly about the confined fixed position thereof. Each of the movable flexure elements has an end fixed with respect to the flexure position of one of the fixed flexure elements and extends therefrom in longitudinally movable and generally transversely confined relation to a receiving portion of an adjacent fixed flexure element the longitudinal outer end of which is adjacent the flexure position thereof. The moving assembly and the cannula assembly are constructed and arranged so that a manual movement of the moving assembly in one direction will effect a movement of the movable flexure elements in an outward direction with respect to the receiving portions associated therewith to extend in an arcuately flexed condition beyond the flexure positions of the fixed flexure elements to cause the latter to flex transversely outwardly and create an expanded condition defined by an annular series of transversely outwardly flexed fixed flexure elements interconnected by an annular series of arcuately flexed portions of the movable flexure elements. The moving assembly and the cannula assembly are constructed and arranged so that a manual movement of the moving assembly in an opposite direction will effect a movement of the movable flexure elements when in the expanded condition in a direction inwardly with respect to the receiving portions associated therewith to cause said expanded condition to progressively retract during which the annular series of transversely outwardly flexed fixed flexure elements are progressively less flexed transversely outwardly and the annular series of arcuately flexed portions of said movable flexure elements have a progressively less arcuate extent.

The positive active expansion and retraction of the extractor of the present invention makes the extractor ideally suited for use in the ureter. The provision of an open distal end rather than a plugged end, as provided in conventional baskets, provides a valuable advantage which cannot be achieved by passively expanding and retracting end plug baskets. The open end capability taken with the positive active expansion capability enables the user to release an overly large captured stone. An overly large stone captured in a passively expanded and retracted end plug basket leaves the operator with no basket-operating capability of releasing the stone in the event it should become desirable to do so. The present invention provides an improved ureter basket which is also useful to solve the problems of kidney stone extraction as well. It will also be understood that the extractor of the present invention is useful in any medical situation where it is desirable to extract matter from interior locations within a patient.

While the particular medical use will determine the proper size, for ureter-kidney use, it is desirable to miniaturize the size as much as possible or at least to the extent of enabling the extractor to be used with a scope having a three French central passage. In accordance with the principles of the present invention, maximum miniaturization is obtained by forming the fixed flexure elements and the tubular portion of the cannula assembly with the use of helically wound wire sections assembled so as to provide longitudinal stability and lateral flexibility.

Another object of the present invention is to provide a cost-effective method of manufacturing an extractor with the utilization of helically wound wire sections. In accordance with the principles of the present invention, this objective is achieved by providing a method of making a medical extractor comprising the initial step of forming a component in the form of a helically wound wire section having (1) a longitudinally stable and transversely flexible end section, (2) a straight wire section extending tangentially from an end loop of the end section, and (3) an adjacent bend in the straight wire section which extends the remainder of the wire section angularly toward the helically wound wire section. A series of the components are secured together in an assembled relation wherein the helically wound wire sections are disposed in a longitudinally stable and transversely flexible annular array with the end sections disposed in generally coextensive independently flexing relation. The straight wire section of each component is inserted within the end section of an adjacent helically wound wire section so as to extend outwardly of the opposite end thereof. Finally, a moving assembly is connected to the opposite ends of the helically wound wire sections and the ends of said straight wire sections extending outwardly thereof, so that the straight wire sections can be moved with respect to the helically wound wire sections.

These and other objects of the present invention will become more apparent during the course of the following detailed description and appended claims. The invention may best be understood with reference to the accompanying drawings wherein an illustrative embodiment is shown.

DESCRIPTION OF THE DRAWINGS

FIG. 1 is a perspective view of the distal end portion of a cannula assembly of one embodiment of a medical extractor which is constructed in accordance with the principles of the present invention, showing the annularly expanding and retracting gripping and releasing mechanism in a retracted insertion position;

FIG. 2 is a view similar to FIG. 1, showing the gripping and releasing mechanism of the extractor in an expanded maximum deployed position;

FIG. 3 is a sectional view of the proximal end portion of the cannula assembly connected with a moving assembly of the medical extractor of FIG. 1, showing the components in an insertion position;

FIG. 4 is a view similar to FIG. 3 showing the components in a maximum deployed position;

FIG. 5 is an enlarged sectional view taken along the line 5—5 of FIG. 3;

FIG. 6 is an enlarged sectional view taken along the line 6—6 of FIG. 3;

FIG. 7 is a perspective view of the distal end portion of another embodiment of a cannula assembly of a medical extractor which is constructed in accordance with the principles of the present invention, showing the gripping and releasing mechanism of the extractor in a retracted insertion position;

FIG. 8 is a view similar to FIG. 7, showing the gripping and releasing mechanism in an expanded maximum deployed position;

FIG. 9 is a view similar to FIG. 7, showing the gripping and releasing mechanism in a gripping position with an object;

FIG. 12 is a vertical sectional view of the distal end portion of a cannula assembly of still another form of a medical extractor which embodies the principles of the present invention, showing the gripping and releasing mechanism of the extractor in a retracted insertion position;

FIG. 13 is a view similar to FIG. 12, showing the gripping and releasing mechanism in an expanded maximum deployed position;

FIG. 14 is a sectional view of the proximal end portion of the cannula assembly connected with a moving assembly of the extractor of FIG. 12, showing the components in an insertion position;

FIG. 15 is a sectional view taken along the line 15—15 of FIG. 14;

FIG. 16 is a sectional view taken along the line 16—16 of FIG. 14;

FIG. 17 is a sectional view taken along the line 17—17 of FIG. 14;

FIG. 18 is an enlarged sectional view taken along the line 18—18 of FIG. 14;

FIG. 24 is a vertical sectional view of the distal end of a cannula assembly of still another medical extractor which embodies the principles of the present invention, showing the gripping and releasing mechanism of the extractor in a retracted insertion position;

FIG. 25 is a view similar to FIG. 24, showing the gripping and releasing mechanism in an expanded maximum deployed position and the fiber optic probe in phantom in an operating position;

FIG. 26 is a sectional view of the proximal end portion of the cannula assembly connected with a moving assembly of the extractor of FIG. 24, showing the components in an insertion position;

FIG. 27 is a sectional view taken along the line 27—27 of FIG. 26;

FIG. 28 is a sectional view taken along the line 28—28 of FIG. 26;

FIG. 29 is a sectional view taken along the line 29—29 of FIG. 26; and

FIG. 30 is an enlarged sectional view taken along the line 30—30 of FIG. 26.

DETAILED DESCRIPTION OF THE PREFERRED EMBODIMENTS OF THE INVENTION

Figure 10:
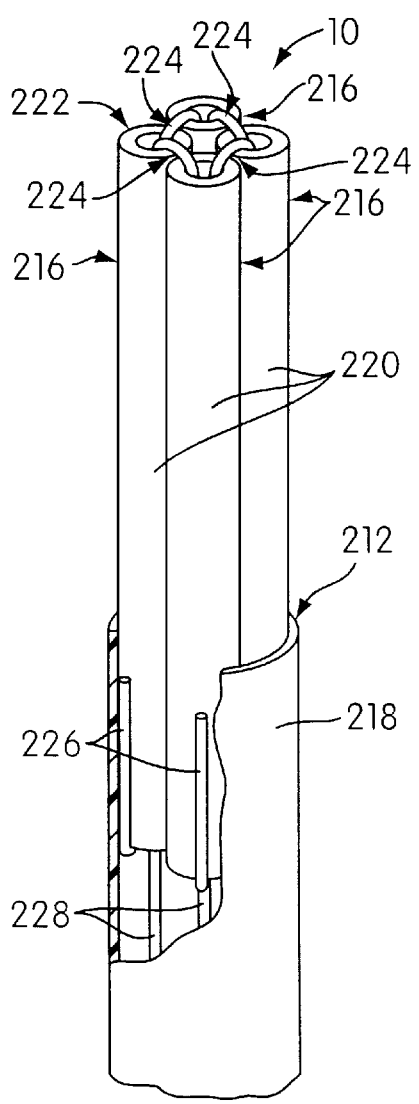
FIG. 10 is a view similar to FIG. 1 of the distal end portion of another embodiment of a cannula assembly of a medical extractor which embodies the principles of the present invention showing the gripping and releasing mechanism thereof in a retracted insertion position.

Referring now more particularly to FIGS. 1–6 of the drawings, there is shown therein one embodiment of a medical extractor, generally indicated at 10, which embodies the principles of the present invention. The embodiment shown is particularly constructed to be used in a percutaneous kidney stone extraction procedure. The medical extractor 10 includes, in general, an elongated cannula assembly, generally indicated at 12, and a moving assembly, generally indicated at 14, operatively connected with the proximal end portion of the cannula assembly 12.

The cannula assembly 12 is essentially constructed as an elongated wall structure providing a generally smooth exterior periphery and a hollow interior. In the embodiment shown, the elongated wall structure is formed by four coextensive side-by-side flexible tubular members, generally indicated at 16 disposed in an annular array. The tubular members 16 are formed of a suitable plastic material such as polyethylene, polypropylene, polyester, polyvinyl chloride, polyimide or the like. For the percutaneous application shown, the four tubular members 16 are encased within a thin walled outer tubular member 18. The outer tubular member 18 is preferably relatively flexible and is formed of a suitable relatively flexible plastic material although a rigid metal material can be utilized if desired.

At the distal end of the cannula assembly 12, the flexible tubular members 16 extend outwardly of the distal end of the outer tubular member 18. The outwardly extending distal end sections of the flexible tubular members 16 constitute longitudinally fixed flexure elements 20 forming a part of an annularly expanding and retracting gripping and releasing mechanism, generally indicated at 22, at the distal end of the cannula assembly 12.

The cannula assembly 12 also includes four wires or rodular members, generally indicated at 24. The wires 24 are preferably made of stainless steel, although other materials both electrically conducting and otherwise may be used. Each wire 24 has a length in excess of twice the length of the flexible tubular members 16. As shown, each wire 24 is bent at a midportion thereof so as to define a fixed wire section 26 and a movable wire section 28.

The four fixed wire sections 26 extend within the four flexible tubular members 16 with the bend being disposed in a flexure position on the longitudinally fixed flexure elements 20 which, as shown, is at the distal free ends of the tubular members 16. The four fixed wire sections 26 are fixed with respect to the four tubular members 16 within which they extend in a manner hereinafter to be more fully explained.

The four movable wire sections 28 also extend within the four tubular members 16, however, not within the same tubular members 16 as the fixed sections 26; but, instead, in adjacent tubular members 16. Each movable wire section 28 extends from the bend which connects it to the associated fixed wire section 26 through its associated tubular member 16 and outwardly beyond the proximal end thereof.

The preferred embodiment of the moving assembly 14 shown in FIGS. 3–5 includes a main body, generally indicated at 30, molded of a suitable plastic or metal material. The main body 30 is of generally tubular construction and of a size to be conveniently gripped in one hand. The main body 30 is formed of a peripheral wall 32 having an end wall 34 at a forward end thereof. The rearward end of the peripheral wall 32 is enlarged and exteriorly threaded, as indicated at 36. An elongated slot 38 is formed in the peripheral wall 32 which extends rearwardly from the forward end wall 34 thereof, completely through the enlarged rear end thereof.

The forward end wall 34 is centrally apertured to receive therethrough the end portions of the movable wire sections 28 which extend beyond the normal ends of the flexible tubular members 16. The forward end wall 34 has its forward extremity shaped into a frusto-conical exterior surface 40 and an intermediate portion is formed with exterior threads as indicated at 42. The exterior frusto-conical surface 40 is sized to cooperate with an interior frusto-conical surface 44 formed on a mounting element, generally indicated at 46, in the form of an interiorly threaded cap. The cap mounting element 46 is centrally apertured to receive therethrough the outer tubular member 18 so as to be capable of being initially moved over the proximal end of the outer tubular member 18. The cap mounting element 46 when threaded on the threads 42 of the end wall 34 serves to secure the proximal ends of the fixed wire sections 26, the proximal ends of the tubular members 16 and the proximal end of the outer tubular member 18 to the main body 30 of the moving assembly 14.

It will be understood, that the securement can be effected by splitting the proximal end of each tubular member 16 and spreading the split end over the exterior frusto-conical surface 40 so that the contained end of the fixed wire section 26 also engages the exterior frusto-conical surface 40 and thereafter spreading a split proximal end of the outer tubular member over the spread out inner tubular member split ends. As the cup mounting element 14 is thereafter turned on the threads 42, the interior frusto-conical surface 44 of the cap mounting element 46, the proximal ends of the wire sections 26 and inner tubular members 16 in engagement with the exterior frusto-conical surface 40 and the proximal end of the outer tubular member 18 in engagement with the interior frusto-conical surface 44 will be squeezed between the exterior and interior frusto-conical surfaces 40 and 46 until all ends are securely held therebetween.

The ends of the movable wire sections 28 which extend beyond the proximal ends of the inner tubular members 16 pass through the central aperture in the end wall 34 and then extend through a small thin walled tube 48 fixed at its forward end within the end wall 34 in alignment with the central aperture of the end wall 34. The tube could be molded integral with the main body 30 although a separate fixed tube is preferred because of its thin wall construction. The thin walled tube 48 extends within a cylindrical through bore 50 formed centrally within a moving member, generally indicated at 52.

The moving member 52 has its exterior shaped into a generally cylindrical configuration so as to slidably engage within the interior of the peripheral wall 32 as the bore 50 slidably engages the exterior of the thin walled tube 48. The moving member 52 moves in opposite longitudinal directions between an insertion position, as shown in FIG. 4 and a maximum deployed position, as shown in FIG. 5. The moving member 52 includes an upstanding digitally engageable portion 54 which extends upwardly through the slot 38 in the main body 30. The digitally engageable portion 54 includes a projection 56 at its forward end for facilitating the digital movement of the movable member 52 in both longitudinal directions with respect to the main body 30.

The rear end portion of the moving member 52 is formed with a frusto-conical exterior surface 58 over which the terminal ends of the movable wire sections 28 are bent when the movable member 52 is disposed in its insertion position. A mounting element 60 in the form of a threaded cap with an interior frusto-conical surface, similar to the cap moving element 46, is threadedly engaged on the end of the moving member 52 to securely fix the movable wire sections 28 thereto.

An end cap 62 is threadedly mounted on the threads 36 at the rear end of the main body 30. The end cap 62 includes a forwardly extending inner annular portion which enters within an interior groove in the rear end of the peripheral wall 32 to maintain the diametrical integrity of the peripheral wall 32. The end cap 62 is constructed so as to permit cap mounting member 60 to freely enter therein with no air lock action; as, for example, by including an oversize bore. It will be understood that the end cap could be centrally apertured or provided with one or more longitudinal grooves in its bore, if made full size, to accomplish the same function.

In the use of the medical extractor 10 in a percutaneous kidney stone removal procedure, the standard preparatory procedures and standard auxiliary equipment are used. Initially, a suitable percutaneous tract to the kidney in the patient's body is provided and an adequate visualization of the collecting system of the kidney by means of a scope is established through the percutaneous track. Next, the distal end portion of the cannula assembly 12 is advanced through the scope with the moving member 52 and the annularly expanding and retracting gripping and releasing mechanism 22 of the medical extractor 10 both in the retracted insertion position, as shown in FIGS. 4 and 1 respectively. The advance is continued until the distal end of the cannula assembly 12 reaches the targeted area where the stone is to be removed. This advance is accomplished manually feeding the cannula assembly 12 through the working channel in the scope. As soon as the distal end of the cannula assembly 12 reaches the desired area as determined by visual inspection of the scope, the operator grasps the exterior of the main body 30 of the moving assembly 14 and moves his thumb forward on the digitally engageable portion 54 so as to move the moving member 52 away from the insertion position thereof, shown in FIG. 3, toward the maximum deployed position thereof, shown in FIG. 4. The extent of the forward movement is sufficient to expand the mechanism 22 to engage the stone to be extracted.

As the moving member 52 is moved forward, the proximal ends of the movable wire sections 28 are moved therewith. Since the movable wire sections 28 are captured peripherally throughout their extent, the movement of their proximal ends with the moving member 52 causes their opposite distal ends to move outwardly of the distal ends of the flexible tubular members 16 or the fixed flexure elements 20. Since the distal ends of the movable wire sections 28 are fixed to the adjacent fixed flexure elements 20 by virtue of the fixture of the integral fixed wire section 26 therewith, the movement of the distal end portions of the movable wire sections 28 outwardly of the fixed flexure elements 20 which contain them causes the fixed flexure elements 20 to be flexed radially outwardly at their free ends and the outwardly extending end portions of the movable wire sections 28 to flex arcuately outwardly beyond the distal free ends of the fixed flexure elements 20.

When the moving member 52 reaches the deployed position, as shown in FIG. 4, the outwardly extending distal end portions of the movable wire sections 28, which constitute longitudinally movable flexure elements 64, are in arcuate configurations outwardly of the flexure positions of the fixed flexure elements 20, as shown in FIG. 2. It can be seen that the flexure position of each fixed flexure element 20 is biased outwardly by two associated movable flexure elements 64, one of which is integrally connected with the fixed wire section 26 therein and one of which is integral with the movable wire section 28 therein. Since the two movable flexure elements 64 associated with each fixed flexure element 20 have their opposite ends associated with the two adjacent fixed flexure elements 20, the flexural movement is imposed symmetrically upon each fixed flexure element 20 by the associated movable flexure elements 64. The result is that the gripping and releasing mechanism 22 expands annularly from its retracted insertion position, as shown in FIG. 1, both radially outwardly and longitudinally outwardly. In its maximum expanded deployed position, as shown in FIG. 2, the extracting mechanism 22 is defined at its outer portion by four longitudinally outwardly arcuately flexed movable flexure elements 64 extending in an open annular series or array. In the embodiment shown, the movable flexure elements 64 are in the form of wire sections 64 constituting distal sections of the movable wire sections 28, the remaining sections of which form continuing sections of the wire sections 64. The inner portion of the maximally expanded deployed gripping and releasing mechanism 22 is defined by four radially outwardly flexed fixed flexure elements 20 extending from a position of confinement determined by the position of the distal free end of the outer tubular member 18.

The deployment configuration whether maximal or less enables the operator to move the expanded gripping and releasing mechanism 22 longitudinally over the targeted kidney stone until it is captured therein. This longitudinal forward movement is a more natural movement to effect capture of the stone in the kidney's collecting system as compared with a lateral movement. Nevertheless, alternatively, it is possible to loop the most convenient arcuate flexure element 64 over the stone to position it inside the deployed retrieving mechanism 22. During the looping movement, it is noted that the fixed flexure elements 20 which are not associated with the movable flexure element 64 used to loop the stone as well as the three movable flexure elements 64 associated therewith provide structure to engage the stone as the looping movement progresses, thus establishing the full entry of the stone within the extracting mechanism 22. The deployment movement is determined to take place in a coordinated relation with the position of the stone within the kidney collecting system. The advancing longitudinal movement or the looping movement can be a coordinated part of the deployment movement or fully sequential. In this way, either the annular series of outwardly arcuately flexed movable flexure elements 64 are moved around the stone or the selected movable flexure element 64 more or less is reached out and looped over the stone. In this coordinated movement, it is noted that there are no sharp points ever presented to deal with which might start hemorrhaging.

Once the stone is positioned within the expanded gripping and releasing mechanism 22, the operator simply moves the moving member 52 of the moving mechanism 14 rearwardly away from the deployed position toward the insertion position shown in FIG. 3. This rearward movement of the moving member 52 effectively retracts the movable flexure elements 64 back into the fixed flexure elements 20 of the retrieving mechanism 22. As this movement progresses, the arcuate extent of the movable flexure elements 64 becomes smaller and the flexure positions at the free ends of the fixed flexure elements 20 move radially inwardly. This progressive movement has the effect of engaging the stone within the four fixed flexure elements 20. As the movable flexure elements 64 continue to move within the fixed flexure elements 20, the outer portion of the gripping and releasing mechanism 22 is retracted both radially and longitudinally inwardly. The retracting outer portion of the gripping and releasing mechanism 22 including the movable flexure elements 64 and free ends of the fixed flexure elements 20 alternately move into tight gripping engagement with the outer portion of the stone. This tight gripping engagement biases the stone inwardly into a tighter captured relationship within the fixed flexure elements 20.

With the stone thus tightly engaged, the cannula assembly 12 can be withdrawn from the patient outwardly of the installed percutaneous tract. Note that during this fixed withdrawing movement the broader fixed flexure elements 20 are leading.

Referring now more particularly to FIGS. 7–9, it will be understood that the medical extractor 10 can be modified to enable it to be used nephroureteroscopically. FIGS. 7, 8 and 9 illustrate a modified cannula assembly, generally indicated at 112, which has been miniaturized for urinary tract travel and is capable of being substituted in the device 10 for the cannula assembly 12 heretofore described.

The cannula assembly 112 is essentially constructed as an elongated wall structure providing a generally smooth exterior periphery and a hollow interior. In the embodiment shown, the elongated wall structure is formed by three coextensive side-by-side flexible tubular members, generally indicated at 116, disposed in an annular array. The tubular members 116 are formed of a suitable plastic material such as polyethylene, polypropylene, polyester, polyvinyl chloride, polyimide or the like. For the nephroureteroscopic application shown, the three tubular members 116 are fused together from the proximal ends thereof up to a confined position, indicated at 118 in FIGS. 7–9, spaced from the distal ends thereof.

At the distal end of the cannula assembly 112, the flexible tubular members 116 extend outwardly of the confined position 118. The outwardly extending distal end sections of the flexible tubular members 116 constitute longitudinally fixed flexure elements 120 forming a part of an annularly expanding and retracting gripping and releasing mechanism, generally indicated at 122, at the distal end of the cannula assembly 112.

The cannula assembly 112 also includes three wires or rodular members, generally indicated at 124. The wires 124 are preferably made of stainless steel although other materials both electrically conducting and otherwise may be used. Each wire 124 has a length in excess of twice the length of the flexible tubular members 116. As shown, each wire 124 is bent at a midportion thereof so as to define a fixed wire section 126 and a movable wire section 128.

The three fixed wire sections 126 extend within the three flexible tubular members 116 with the bend being disposed in a flexure position on the longitudinally fixed flexure elements 120 which, as shown, is at the distal free ends of the tubular members 116. The three fixed wire sections 126 are fixed with respect to the three tubular members 116 within which they extend in a manner hereinafter to be more fully explained.

The three movable wire sections 128 also extend within the three tubular members 116, however, not within the same tubular members 116 as the fixed sections 126; but, instead, in adjacent tubular members 116. Each movable wire section 128 extends from the bend which connects it to the associated fixed wire section 126 through its associated tubular member 116 and outwardly beyond the proximal end thereof.

The cannula assembly 112 is connected with the moving assembly 14 in the same manner as the cannula assembly 12. The expanding and retracting echanism 122 is moved between retracted insertion and extended maximum deployed positions by the moving assembly 14 in the same manner as previously described. The difference in operation lies in the manner of gaining access to the kidney area.

It is noted that the construction of the cannula assembly 112 lends itself to miniaturization and flexibility, both qualities required to enable the distal end of the cannula assembly 112 containing the retrieving mechanism 122 to reach the kidneys through the urinary tract. Once the kidney area has been reached, the operation is the same as previously described.

Figure 11:
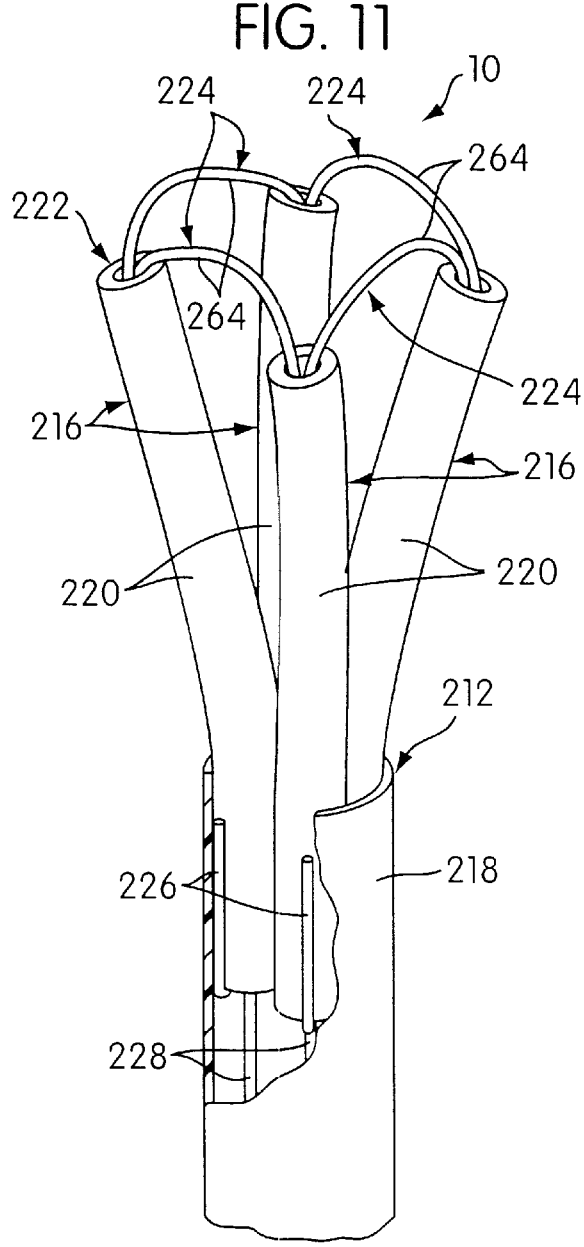
FIG. 11 is a view similar to FIG. 10 showing the gripping and releasing mechanism in an expanded maximum deployed position.

Referring now more particularly to FIGS. 10 and 11 of the drawings, there is shown therein a modification of the medical extractor 10 which renders it particularly useful in a ureteroscopic stone extraction procedure. FIGS. 10 and 11 illustrate a modified elongated cannula assembly, generally indicated at 212, which can be used instead of the cannula assembly 212 with the moving assembly 214.

The cannula assembly 212 is essentially constructed as an elongated wall structure providing a generally smooth exterior periphery and a hollow interior. In the embodiment shown, the elongated wall structure is formed by a single flexible tubular member, generally indicated at 216. The tubular member 216 is formed of a suitable plastic material such as polyethylene, polypropylene, polyester, polyvinyl chloride, polyimide or the like.

At the distal end of the cannula assembly 212 as indicated at 218, the flexible tubular member 216 fixedly receives end sections of four longitudinally fixed flexure elements 220 forming a part of an annularly expanding and retracting gripping and releasing mechanism, generally indicated at 222, at the distal end of the cannula assembly 212.

The cannula assembly 212 also includes four wires or rodular members, generally indicated at 224. The wires 224 are preferably made of stainless steel, although other materials both electrically conducting and otherwise may be used. As shown, each wire 224 is bent at a position spaced from one end a distance slightly greater than the length of the fixed flexure elements 220 so as to define a relatively short fixed wire section 226 and a relatively long movable wire section 228 having a length greater than the tubular member 216.

The four fixed wire sections 226 extend within the four fixed flexure elements 220 with the bend being disposed in a flexure position on the longitudinally fixed flexure elements 220 which, as shown, is at the distal free ends thereof. The free end portions of the four fixed wire sections 226 extend through the four fixed flexure elements 220 and are bent back over the outer peripheries of the associated four flexure elements 220 to an extent necessary to secure them between the interior periphery of the tubular member 216 and the coextensive exterior peripheries of the four fixed flexure elements which are likewise secured at the position of confinement 218.

The four movable wire sections 228 also extend within the four fixed flexure elements 220, however, not within the same fixed flexible element 220 as the fixed sections 226; but, instead, in adjacent fixed flexible elements 220 and through the tubular member 216 and outwardly beyond the proximal end thereof.

The cannula assembly 212 is connected with the moving assembly 14 in the same manner as the cannula assembly 12 except that only the proximal end of the single tubular member 218 is fixed between the frustoconical surfaces 40 and 44. The gripping and releasing mechanism 222 is moved between retracted insertion and extended maximum deployed positions by the moving assembly 14 in the same manner as previously described.

The extractor 10 with the cannula assembly 212 is used in a ureteroscopic stone retrieval procedure, after the scope has been extended through the urinary tract and encountered a stone. The cannula assembly 212 is then advanced through the scope to the region of the stone with the expanding and retracting extracting mechanism 222 in its retracted insertion position. The advance continues until the distal tip of the expanding and retracting extracting mechanism 222 extends along the wall of the ureter beyond the stone. Thereafter, the gripping and releasing mechanism 222 is deployed in the manner previously described. After deployment, the stone is engaged by moving the deployed mechanism 222 rearwardly with the movable flexure element 264 between the ureteral wall and the stone, thus positioning the stone in the radially outwardly flexible fixed flexure elements 220. Once the stone is engaged, it is secured in the manner previously described.

It can be seen that the manner of utilizing the cannula assembly 212 is generally similar to the anner in which conventional wire baskets are utilized. However, the open forward end and active expansion of the present gripping and retrieving mechanism 222 allows the operator to disengage from a stone after the stone has been captured. This desirable function, which is lacking in conventional wire baskets, can become important to prevent certain surgical complications; such as ureter avulsion or retained basket. Moreover, the characteristics of the present gripping and retrieving mechanism 222 which achieves the function also renders the extractor 10 more suitable to extracting impacted ureteral meatal stones because of the lack of an end plug such as is embodied in conventional baskets. Indeed, the extractor 10 of the present invention can be used in lieu of conventional wire baskets in all indications in addition to its use in lieu of conventional graspers. When used as either a grasper or a basket, an active expansion is provided which is not available in either conventional baskets or graspers.

It will be understood that the differently constructed cannula assemblies 12, 112 and 212 are not limited in their application to the procedures described therewith. Each could be used in any of the described procedures. In addition, each of the differently constructed cannula assemblies 12, 112 and 212 could be customized to perform an extracting procedure for medical usages such as removal of a foreign body or other material from a bronchus, removal of an object from the stomach, removal of a tumor from the bowel, removal of a stone from the biliary tract, plaque and/or clots from arteries or veins or any object from any body part.

The disclosed manner of securing the ends of the movable flexure elements 64 (or 164 or 264) to the fixed flexure elements 20 (or 120 or 220) is desirable in that it is economical and accommodates miniaturization very well. Other well known modes of securement may be used especially when larger annular sizes can be used. For example, where the fixed flexure elements 20 (or 120 or 220) are molded rather than be assembled from extruded tubing, the wire ends can be embedded therein as inserts in the mold.

It is important to note that the gripping and releasing mechanism 22 (or 122 or 222) of the present invention provides both active expansion and active retraction. That is, both expansion and retraction are actively under the control of the physical movement of structural wires. This active expansion is in contrast with expansion which takes place by virtue of metal memory or retraction which ends with a collapsed balloon. The intensity and extent of expansion can be varied by the selection of materials of the flexure elements 20 (or 120 or 220) and 64 (or 164 or 264), the selected diameter sizes and length of the fixed flexure elements 20 (or 120 or 220) and the selected diameter sizes and length of movement of the movable flexure elements 64 (or 164 or 264). The fixed flexure elements 20 (or 120 or 220) could be a spiral wire rather than a tube the essential characteristic being that each movable flexure element 64 (or 164 or 264) is transversely contained between the confined fixed position and the flexure position of the associated fixed flexure element 20 (or 120 or 220) in the sense of preventing the movable flexure element 64 (or 164 or 264) from bulging transversely outwardly in any direction to an extent sufficient to effect its proper arcuately outward flexure during operation.

The exact configuration of the gripping and releasing mechanism 22 (or 122 or 222) when in its maximum expanded deployed position will depend upon the relative flexure characteristics of the fixed flexure elements 20 (or 120 or 220) with respect to the movable flexure elements 64 (or 164 or 264). Where the movable flexure elements flex more readily than the fixed flexure elements, the latter tend to remain with their free ends displaced only radially outwardly as is the case with the fixed flexure elements 120 and movable flexure elements 164 in the cannula assembly 1122 of FIGS. 7–9. In this case, the movable flexure elements do not have much tendency to move the free ends of the fixed flexure elements in an annular direction in addition to the radially outward direction. However, as the relative flexure characteristics are changed to a relationship in which the fixed flexure elements are more readily flexed than the movable flexure elements, the movement of the fixed flexure elements become more influenced by the flexure characteristics of the movable flexure elements. In this case, the free ends of the fixed flexure elements will have a significant annular movement in addition to their radially outward movement when reaching the maximum expanded deployed position as is the case with the cannula assemblies 12 and 212 of FIG. 1–6 and 10–11. The result is that the fixed flexure elements each assume a more or less spiral configuration.

It will be understood that the terms "fixed" and "movable" used to identify the two different flexure elements 20 (or 120 or 220) and 64 (or 164 or 264) are used in the relative sense. That is, while the moving assembly 14 is operable to move the movable flexure elements 64 (or 164 or 264) with respect to the main body 30 of the moving assembly 14 and the fixed flexure elements 20 (or 120 or 220), it is within the contemplation of the present invention to utilize a conventionally known moving assembly in which the fixed flexure elements 20 (or 120 or 220) are moved with respect to the main body of the moving assembly 14 and the movable flexure elements 64 (or 164 or 264). In this case, the movable flexure elements 64 (or 164 or 264) still have relative movement with respect to the tubular cannula structure 12 (or 112 or 212) and the fixed flexure elements 20 (or 120 or 220) are still fixed with respect to the tubular cannula structure 12 (or 112 or 212). It is in this latter relative sense that the terms are used.

Referring now more particularly to FIGS. 12–14 of the drawings, there is shown therein a medical extractor, generally indicated at 310, which embodies the principles of the present invention. The embodiment shown is particularly constructed to be used in a nephroureteroscopic kidney stone retrieval procedure. The medical extractor 310 includes, in general, an elongated cannula assembly, generally indicated at 312, and a moving assembly, generally indicated at 314, operatively connected with the roximal end portion of the cannula assembly 312.

The cannula assembly 312 is essentially constructed as an elongated wall structure providing an exterior periphery suitable to pass through the scope passage and a hollow interior. In the embodiment shown, the elongated wall structure is formed by a central flexible rodular member 316 and helical members 320 in the form of helically wound wire sections 320 positioned annularly therearound. The rodular member 316 is preferably formed of a suitable plastic material such as polyethylene, polypropylene, polyester, polyvinyl chloride, polyimide or the like. For the nephroureteroscopic application shown, there are four spaced helical members 320 fused within the exterior periphery of the central rodular member 316. The helically would wire sections 320 are preferably made of stainless steel wire with a loop size just sufficient to allow passage of the wire loosely therethrough and a pitch which is several times the wire diameter, as, for example, four. While the plastic stainless steel construction is preferred, it is within the contemplation of the present invention to form the rodular member 316 of metal and effect a solder, brazing or welding connection thereof with the helical members. It is also contemplated that a plastic rodular member could be strengthened by utilizing a metal wire core.

At the distal end of the cannula assembly 312, the helical members 320 extend outwardly of the distal end of the central rodular member 316. The outwardly extending distal end portions of the helical members 320 are preferably changed in pitch to one which is equal to approximately 1½ times the wire diameter. The outwardly extending distal end sections of the helically wound wire sections 318 constitute longitudinally fixed flexure elements 322 forming a part of an annularly expanding and retracting gripping and releasing mechanism, generally indicated at 324, at the distal end of the cannula assembly 312.

The cannula assembly 312 also includes four movable wire sections 326 which are preferably made a continuation of the stainless steel wire which is used to form the fixed flexure elements 322. Each wire section 326 has a length in excess of the length of the helically wound wire sections 320. As shown, each movable wire section 326 is bent at an integral juncture thereof with the distal end of the associated fixed flexure element 322. The integral juncture between the proximal end of each fixed flexure element 322 and the distal end of the remainder of the associated helically would wire section 320 is reinforced by a plastic tape 328 or the like. The taped area constitutes a fixed position of confinement of the cannula assembly 312 from which the fixed flexure elements 322 extend. The fixed position of confinement preferable is achieved by plastic fusion or adhesive bonding without increasing the exterior diameter of the annular array.

In addition, in order to prevent the helical wire which forms each fixed flexure element 322 from expanding or contracting in a longitudinal direction, a plastic tape or painted on body of plastic, indicated at 329, is provided on an annular outer sector of each fixed flexure element 322. The plastic 329 extends thinly over the outer periphery of the loops or volutes of the helically wound wire section and between adjacent volutes. The sector configuration of the plastic 329 enables the inner portions of the volutes of the helically wound wire section to expand or contract so that the fixed flexure elements 322 can flex arcuately outwardly as the gripping and releasing mechanism 324 is expanded.

The wire used to form the helically wound wire sections 330 can be initially coated with a very thin layer of plastic. The coating makes the fusion with the central tubular member 316 and the tape 329 a plastic to plastic fusion and provides the fixed flexure elements 322 with a plastic gripping surface. Alternatively, the inner peripheral portion of the volutes of the helically wound wire section forming each fixed flexure element 322 can be coated with plastic to provide a gripping surface with a better coefficient of friction than stainless steel.

The four wire sections 326 extend within the four helically wound wire sections 320 with the bend being disposed in a flexure position on the longitudinally fixed flexure elements 322 which, as shown, is at the distal free ends of the helically wound wire sections 320. The four movable wire sections 326 are fixed with respect to the four helically wound wire sections 320 by virtue of being an integral part thereof.

The four movable wire sections 326 extend within the four helically wound wire sections 320, however, not within the same helically wound wire sections 320 to which they are fixed; but, instead, in adjacent helically wound wire sections 320. Each movable wire section 326 extends from the bend which connects it to its helically wound wire section 320 through an associated adjacent helically wound wire section 320 and outwardly beyond the proximal end thereof.

The preferred embodiment of the moving assembly 314 shown in FIGS. 14–18 includes a main body, generally indicated at 330, molded of a suitable plastic material or formed of a metal material. The main body 330 is of generally tubular construction and of a size to be conveniently gripped in one hand. The main body 330 is formed of a peripheral wall 332 having an end wall 334 at a rearward end thereof. The forward end of the peripheral wall 332 is exteriorly threaded, as indicated at 336. An elongated slot 338 is formed in the peripheral wall 332 which extends rearwardly from the forward end thereof to a position spaced from the rear wall 334.

Mounted within the interior of the peripheral wall 332 is an insert member, generally indicated at 340. The insert member 340 includes a main body portion 342 which is configured to fit within the forward end of the peripheral wall 332 and the coextensive portion of the slot 338. The insert member 340 also includes a flange-like portion 344 disposed forwardly of the main body portion 342 which is shaped to engage an inner annular portion of the forward edge of the peripheral wall 332.

Extending forwardly from a central portion of the flange-like portion 344 is a forwardly projecting portion 346 which forms a bendable transmission between the rigid main body 330 of the moving assembly 314 and the more flexible cannula assembly 312. The projecting portion 346 terminates forwardly in a scope channel sealing extremity having an exterior periphery 348 which is shaped to cooperate with the movable seal of the scope.

The sealing extremity also includes (1) a central opening 350 sized to receive a proximal end portion of the central rodular member 316 therethrough which extends rearwardly from the main body of the central rodular member 316 fused to the helically wound wire sections 320, and (2) four annularly spaced openings 352 sized to receive therethrough the proximal end portions of the four movable wire sections 326 extending from the terminal proximal ends of the four helically wound wire sections 320 which are disposed in abutting relation to the forward face of the sealing extremity of the projection portion 346.

The short central opening 350 communicates rearwardly with a central opening 354 which extends rearwardly through the insert member 340 including a cylindrical rearward extension portion 356 thereof. The central opening 354 has the shape of a plus with the cross at the center expanded circularly. Stated differently, the opening 354 includes a center portion sized to receive therein the central rodular member 316 and four annularly spaced radiating grooves sized to receive the four movable wire sections 326 therein.

It will be understood that the position of the sealing surface 348 from the distal end of the cannula 312 is related to the length of the scope so that it will enter the proximal end of the working channel of the scope when the extracting mechanism 324 of the extractor 310 extends from the distal end of the working channel of the scope.

A cap mounting element 358 is centrally apertured to receive therethrough the forward projecting portion 346 so as to be capable of being initially fed forwardly over the proximal end portion of the cannula assembly 312 and then moved rearwardly over the projecting portion 346. The cap mounting element 358 is interiorly threaded to engage with the threads 336 of the peripheral wall 332. When so threadedly engaged, the mounting element 558 serves to secure the insert member 340 and projecting portion 346 to the main body 330.

The cylindrical rearward extension portion 356 of the insert member 340 slidably extends within a central cylindrical opening 360 extending rearwardly from the forward end of a moving member, generally indicated at 362. The rearward end of the cylindrical opening 360 communicates with an opening 364 which has a configuration the same as the opening 354 to receive the central rodular member 316 and four movable wires 326 therethrough.

The rear end portion of the moving member 362 is formed with a frusto-conical exterior surface 366 over which the terminal ends of the four movable wire sections 326 are bent. A mounting element 368 in the form of a snap-on cap with an interior frusto-conical surface 370 is snap fitted (or threadedly engaged) on the end of the moving member 362 to securely fix the movable wire sections 326 thereto. The cap mounting member 368 is centrally apertured to receive therethrough the proximal end portion of the central rodular member 316.

The moving member 362 includes a cylindrical exterior periphery with an upstanding digitally engageable portion 372 which is sized to move through the slot 338 in the main body 330. The digitally engageable portion 372 includes a projection 374 at its forward end for facilitating the digital movement of the moving member 362 in both longitudinal directions with respect to the insert member 340 and the main body 330 between an insertion position, as shown in FIG. 14, and a maximum deployed position disposed in abutting engagement with the main body 342 of the insert member 340.

The moving member 362 is preferably mounted in the main body 330 in assembled relation with the insert member 340 interconnected with the cannula assembly 312 as aforesaid and with the cap mounting element 368 extended over the cannula assembly 312.

It will be noted that the end wall 334 of the main body 330 is centrally apertured to receive the rearward end of the central tubular member 316 extending rearwardly from the centrally apertured cap 368 when the moving member 362 is fully inserted into abutting engagement with the end wall 334.

As shown, the end wall 334 has an annular extension 376 extending rearwardly therefrom capable of receiving the terminal end of the central rodular member 316 therethrough. The rearward end of the annular extension 376 is split to form movable annular gripping elements 378. A cap 380 is provided to fix the proximal end of the central rodular member 316 to the end wall 334 of the main body 330. As shown, the annular extension 376 is exteriorly threaded and the cap 380 includes an interiorly threaded skirt 382 capable of being threadedly engaged on the threads of the annular extension 376. The cap 380 also includes an interior frusto-conical surface 384 which mates with exterior segmental frusto-conical surfaces on gripping elements 378. when the cap 380 is screwed onto the threads of the annular extension 376, the gripping elements 378 are cammed into gripping engagement with the periphery of the rodular member 316. In this way, the entire tubular structure of the cannula assembly 312 is fixed to the main body 330 of the moving assembly 314.

In the use of the medical extractor 310 in a nephroureteroscopic kidney stone removal procedure, the standard preparatory procedures and standard auxiliary equipment are used. Initially, a scope is fed through the urinary tract to the kidney in the patient's body and an adequate visualization of the collecting system of the kidney is established by means of the scope and the stone is identified. Next, the distal end portion of the cannula assembly 312 is advanced through the working channel of the scope with the moving member 370 and the gripping and releasing mechanism 324 of the medical extractor 310 both in the retracted insertion position, as shown in FIGS. 14 and 12, respectively. The advance is continued until the distal end of the cannula assembly 312 reaches the targeted area where the stone is to be removed. This advance is accomplished manually feeding the cannula assembly 312 through the working channel in the scope. As soon as the distal end of the cannula assembly 312 reaches the desired area as determined by visual inspection through the scope, the operator grasps the exterior of the main body 330 of the moving mechanism 314 and moves his thumb forward on the digitally engageable portion 372 so as to move the moving member 362 forwardly away from the insertion position thereof, shown in FIG. 14, toward the maximum deployed position thereof. The extent of the forward movement is sufficient to expand the gripping and releasing mechanism 324 to a condition larger than the stone.

As the moving member 362 is moved forward, the proximal ends of the movable wire sections 326 are moved therewith. Since the movable wire sections 326 are captured peripherally throughout their extent, the movement of their proximal ends with the moving member 362 causes their opposite distal ends to move outwardly of the distal ends of the flexible helically wound wire sections 320 or the fixed flexure elements 322. Since the distal ends of the movable wire sections 326 are fixed to the adjacent fixed flexure elements 322, the movement of the distal end portions of the movable wire sections 326 outwardly of the fixed flexure elements 322 which contain them causes the fixed flexure elements 322 to be flexed radially outwardly at their free ends and the outwardly extending end sections of the movable wire sections 326 to flex arcuately outwardly beyond the distal free ends of the fixed flexure elements 322.

When the moving member 362 reaches the desired deployed position, as aforesaid, the outwardly extending distal end sections of the movable wire sections 326, which constitute longitudinally movable flexure elements 386, are in arcuate configurations outwardly of the flexure positions of the fixed flexure elements 322, as shown in FIG. 13. Thus, the movable flexure elements 386 are formed of wire sections 386 with the remainder of the movable wire sections 326 constituting continuing sections of the wire sections 386.

It can be seen that the flexure position of each fixed flexure element 322 is biased outwardly by two associated movable flexure elements 386, one of which is integrally connected therewith and one of which is movable therein. Since the two movable flexure elements 386 associated with each fixed flexure element 322 have their opposite ends associated with the two adjacent fixed flexure elements 222, the flexural movement is imposed symmetrically upon each fixed flexure element 322 by the associated movable flexure elements 386. The result is that the gripping and releasing mechanism 324 expands from its retracted insertion position, as shown in FIG. 12, both radially outwardly and longitudinally outwardly. In its maximum expanded deployed position, as shown in FIG. 13, the gripping and releasing mechanism 324 is defined at its outer portion by four longitudinally outwardly arcuately flexed movable flexure elements 386 extending in an open annular series or array. The inner portion of the maximally expanded deployed mechanism 324 is defined by four radially outwardly flexed fixed flexure elements 322 extending from a position of confinement determined by the position of the distal free end of the central rodular member 316 and tape 329.

The deployment configuration whether maximal or less enables the operator to move the expanded gripping and releasing mechanism 324 longitudinally over the targeted kidney stone until it is lying within the fixed flexure elements 322. This longitudinal forward movement is a more natural movement to effect capture of the stone in the kidney's collecting system as compared with a lateral movement. Nevertheless, alternatively, it is possible to loop the most convenient arcuate flexure element 386 over the stone to position it inside the deployed extracting mechanism 324. During the looping movement, it is noted that the fixed flexure elements 322 which are not associated with the movable flexure element 386 used to loop the stone as well as the two movable flexure elements 386 associated therewith provide structure to engage the stone as the looping movement progresses, thus establishing the full entry of the stone within the gripping and releasing mechanism 324.

The deployment movement is determined to take place in a coordinated relation with the position of the stone within the kidney collecting system. The advancing longitudinal movement or the looping movement can be a coordinated part of the deployment movement or fully sequential. It can be achieved largely through movements of the scope or otherwise by advancing or retracting the extractor 310 within the working channel of the scope. In this way, either the annular series of outwardly arcuately flexed movable flexure elements 386 are moved around the stone or the selected movable flexure element 386 more or less is reached out and looped over the stone. In this coordinated movement, it is noted that there are no sharp points ever presented to deal with which might start hemorrhaging.

Once the stone is positioned within the expanded gripping and releasing mechanism 324, the operator simply moves the moving member 362 of the moving assembly 314 rearwardly away from the deployed position toward the insertion position shown in FIG. 14. This rearward movement of the moving member 362 effectively retracts the movable flexure elements 386 back into the fixed flexure elements 322 of the extracting mechanism 324. As this movement progresses, the arcuate extent of the movable flexure elements 386 becomes smaller and the flexure positions at the free ends of the fixed flexure elements 322 move radially inwardly. This progressive movement has the effect of engaging the stone within the four fixed flexure elements 322. As the movable flexure elements 386 continue to move within the fixed flexure elements 322, the outer portion of the gripping and releasing mechanism 324 is retracted both radially and longitudinally inwardly. The retracting outer portion of the gripping and releasing mechanism 324 including the movable flexure elements 386 and free ends of the fixed flexure elements 322 alternately move into tight gripping engagement with the outer portion of the stone. This tight gripping engagement biases the stone inwardly into a tighter captured relationship within the fixed flexure elements 322 and thus closer to the open distal end of the central rodular member 316.

The utilization of the helically wound wire sections as the tubular members which form the tubular wall structure of the cannula assembly 312 and the fixed flexure elements 322 secures several advantages. First, the connection between the fixed flexure elements 322 and the movable flexure elements 386 is provided by simply making the movable flexure elements 386 an integral extension of the fixed flexure elements 322. Second, by utilizing stainless steel or similar metal materials, it becomes possible to construct the cannula assembly 312 and the gripping and releasing mechanism 324 of a minimal size. Third, by opening the pitch of the helically wound wire sections, the cannula assembly 312 can be made with a highly desirable flexibility in which the resistance to longitudinal expansion and retraction is provided in the central portion of the cannula assembly 312 where the coils are adhered together while the outer portions can expand and retract as needed by movement between the coils. The longitudinal flexibility is especially fundamental to allowing passage of the cannula assembly 312 through the working channel of the scope in highly angled positions such as the lower pole kidney collecting system.

A fourth advantage is that the open nature of the periphery of the cannula assembly 312 provided by the four helically wound wire sections and the four spaces between them enables the cannula assembly 312 to permit a desirable flow of fluid within the working channel of the scope while the cannula assembly 312 is therein. Flow is desirable to maintain optimal visualization of the operative field as viewed through the scope.

Finally, the most significant advantage is that the combination of all of the above-enumerated advantages are obtained.

It is within the contemplation of the present invention to extend the use of the helically wound wire section teachings to handle the proximal end portions of the movable wire sections 326 extending between the sealing surface 348 of the insert member 340 and the opening 364 in the moving member 362. Either a single helically wound wire section could be used encircling all of the movable wire sections 326 or a helically wound wire section could be used encircling each movable wire section 326. Moreover, in this case, the inherent resiliency normally attributable to helical members made of springy material, such as some plastics or some metals, can be used to effect a bias of the moving member 362 toward either its insertion position, as by a compression coil spring effect, or its maximum deployed position, as by a tension coil spring effect.

The extractor 310 can be used in a ureteroscopic stone retrieval procedure, after the scope has been extended through the urinary tract and encountered a stone. The cannula assembly 312 is then advanced through the scope to the region of the stone with the expanding and retracting extracting mechanism 324 in its retracted insertion position. The advance continues until the distal tip of the expanding and retracting extracting mechanism 324 extends along the wall of the ureter beyond the stone. Thereafter, the extracting mechanism 324 is deployed in the manner previously described. After deployment, the stone is engaged by moving the deployed extracting mechanism 324 rearwardly with the movable flexure element 386 between the ureteral wall and the stone, thus positioning the stone in the radially outwardly flexible fixed flexure elements 322. Once the stone is engaged, it is secured in the manner previously described.

It can be seen that this manner of utilizing the cannula assembly 312 is generally similar to the manner in which conventional wire baskets are utilized. However, the open forward end and active expansion of the present extracting mechanism 324 allows the operator to disengage from a stone after the stone has been captured. This desirable function, which is lacking in conventional wire baskets, can become important to prevent certain surgical complications; such as ureter avulsion and retained basket. Moreover, the characteristics of the present extracting mechanism 324 which achieves the function also renders the extractor 310 more suitable to extracting impacted ureteral meatal stones because of the lack of an end plug such as is embodied in conventional baskets. Indeed, the extractor 310 of the present invention can be used in lieu of conventional wire baskets in all indications in addition to its use in lieu of conventional graspers. When used as either a grasper or a basket, an active expansion is provided which is not available in either conventional baskets or graspers. The extractor 310 is also useful in percutaneous kidney extractor procedures.

The helically wound wire sections 320 utilized in the extractor 310 render it susceptible to a cost-effective method of making. In the embodiment just described, each helically wound wire section 320 and integral straight wire section 326 can be viewed as a component which can be made individually. In making the extractor 310, four such components are individually initially made. Each component prior to assembly is formed of a helically wound wire section 320 having (1) a longitudinally stable and transversely flexible end section 322, (2) a straight wire section 326 extending tangentially from an end loop of the end section 322, and (3) an adjacent bend or kink, indicated at 388, in the straight wire section 326 which extends the remainder of the wire section 326 angularly toward the helically wound wire section 320.

In the embodiment shown, the helically wound wire section 320 and the straight wire section 326 are made from one length of stainless steel wire having a constant diameter dimension. In order to make the helically wound end wire sections 322, which have spaced volutes, longitudinally stable, the strip of plastic 329 is fused across the volutes in the formation of the component. In addition, it is preferable that the last loop of the helically wound end wire sections 322 be closed by the application of an adhesive or solder. The adhesive is applied between the underside of the end of the end coil and the adjacent volute thereunder. This preferred construction strengthens the end of the helically wound end wire section 322 where the expanding and retracting forces are applied by the movable wire sections 326 during operation of the completed extractor 310.

The forming of the adjacent bend 388 is desirable as well in the function of the completed extractor 310. A preferred adjacent bend 388 is such that the remainder of the wire section 326 extends toward the helically wound wire section 320 at an angle of approximately 60°. This formation of the adjacent bend 388 defines the position where the wire section 326 must bend to the maximum extent when the extractor 310 is disposed in its insertion position, as shown in FIG. 12. It is desirable not to initially form the bend 388 so that it will assume this maximum bend position, when relaxed, as is the case with the 60° angle bend shown. The 60° bend leaves an amount of resiliency in wire section 326 which effects a certain amount of spring back toward its initial 60° position as the movable flexure elements 386 are moved outwardly during operation so as to help direct the forces that must be applied in order to effect expansion.

After the components have been formed, a series of the components are secured together in an assembled relation wherein the helically wound wire sections are disposed in a longitudinally stable and transversely flexible annular array with the end sections disposed in generally coextensive independently flexing relation. This securement in the case of the extractor 310 is accomplished by adhering the helically wound wire sections 320 in annular array to the central plastic member 316. This can be accomplished with cement or simply by heat (e.g., electrify the wire sections).

After the assembly is secured together, the straight wire section 326 of each component is inserted within the end section 322 of an adjacent helically wound wire section 320 so as to extend outwardly of the opposite end thereof. Finally, a moving assembly is connected to the opposite ends of the helically wound wire sections 320 and the ends of said straight wire sections 326 extending outwardly thereof so that the straight wire sections 326 can be moved with respect to the helically wound wire sections 320. Both of the last steps can be carried out manually.

An extractor 310 sized to pass through the central cavity of a scope measuring 3 French in diameter can be made of three such components made of 6 mil stainless steel wire. Other wire materials are possible including Nitinal with its desirable memory characteristics.

Figure 20:
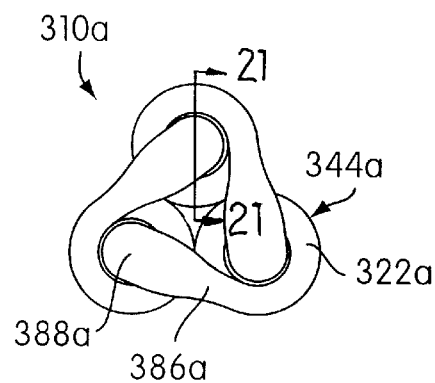
FIG. 20 is a top plan view similar to FIG. 19 of a preferred extractor suitable to function with a scope having a 3 French central cavity.

Referring now more particularly to FIG. 20, there is shown therein a preferred embodiment of an extractor, generally indicated at 310A, which is constructed particularly for use with a scope having a 3 French central cavity. The extractor 310A is made by the same method as previously described, the sole difference is in the construction of each component formed in the first step and that only three components are used instead of four.

Figure 19:
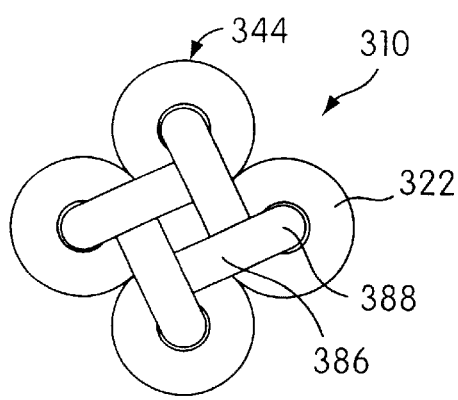
FIG. 19 is a top plan view of the cannula assembly shown in FIG. 12.
Figure 21:
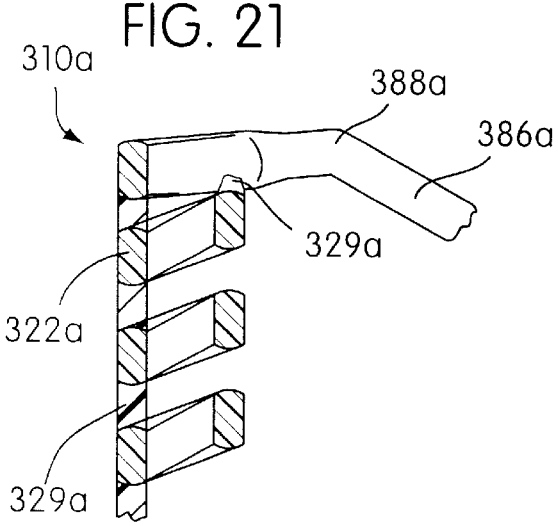
FIG. 21 is a fragmentary cross-sectional view of one component of the extractor of FIG. 20 prior to assembly, the section being taken along the line 21—21 of FIG. 20.

The use of three components serves to provide all of the advantages already noted and, of course, is desirable in miniaturization. In addition, three components achieves a balancing of the annularly applied forces of expansion and retraction. This is particularly desirable when exterior forces are encountered during expansion because of the more stable geometry of a three-sided structure, as compared with the four-sided structures previously described which may tend to distort and close somewhat into a diamond shape. FIG. 20 also illustrates the preferred arrangement of extending the straight wire section 386A tangentially outwardly from the end loop rather than inwardly as shown in FIG. 19. Instead of using one length of wire having the same 6 mil diameter, one length of wire having an initial diameter of 8 mils is used to form each of the three components used. The portion of the length of wire which forms the helically wound wire sections 320A are flattened in a radial direction with respect to the volute formation to a width dimension of approximately 2 mils. This leaves the cross-sectional area essentially the same as the remaining 8 mil diameter section 326A. Other comparable reference numerals with a suffix A are also shown in FIG. 21.

Figure 22:
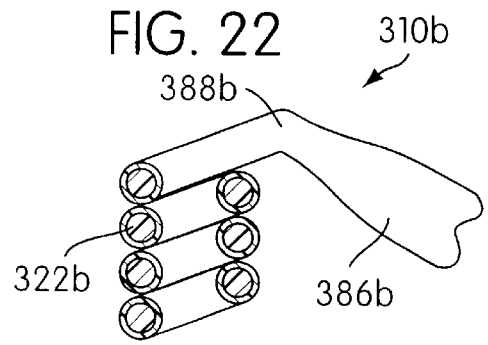
FIG. 22 is a view similar to FIG. 21 showing another component constructed in accordance with the principles of the present invention.

FIG. 22 illustrates another variation of the component construction which can be used. In this embodiment, the portion of the single length of wire which is used to form the helically wound wire section 320B is drawn to a lesser diameter than the remaining straight wire section and the entire length of wire is coated with plastic. In this embodiment, adjacent volutes of the helically wound wire sections 320B are fixed together in abutting relation by cement or by the plastic coated thereon. Alternatively, the coating can be applied after the formation of the helically wound wire sections 320B. When subsequently securing a series of components such as shown in FIG. 22 in an annular array, the plastic coated thereon can be used as heated adhesives to effect the securement, thus omitting the need for a central plastic member and resulting in a hollow central interior which may be used for the passage of a lithotriper probe as hereinafter described in more detail. Alternatively, the coating of the wire sections can be withheld until after assembly so that the coating process also accomplishes the securing process as well.

Figure 23:
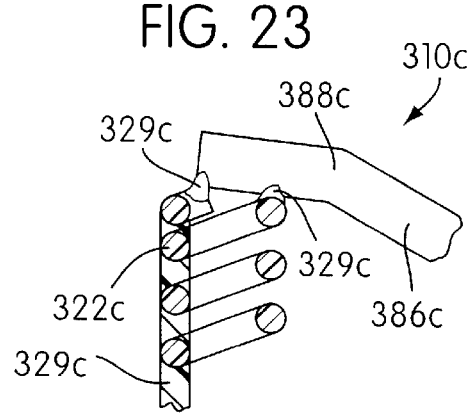
FIG. 23 is a view similar to FIG. 22 showing another component constructed in accordance with the principles of the present invention.

FIG. 23 illustrates still another variation of a component which can be formed in accordance with the principles of the present invention. In this embodiment, the component is formed of two lengths of wire, one of which is of lesser diameter than the other. The lesser diameter wire is used to form the helically wound wire section 320C and the larger diameter wire is used to form the straight wire section 326C with the bend 388C. it will be understood that the two length teachings of the component of FIG. 23 can be applied to the components of FIGS. 19, 21 and 22 and that the abutting volute and coating teachings of the component of FIG. 22 can be applied to the components of FIGS. 19, 21 and 23.

Referring now more particularly to FIGS. 24 and 25 of the drawings, there is shown therein a medical extractor, generally indicated at 410, which embodies the principles of the present invention. The embodiment shown is particularly constructed to be used in a nephroureteroscopic kidney stone retrieval procedure. The extractor device 410 includes, in general, an elongated cannula assembly, generally indicated at 412, and a moving assembly, generally indicated at 414, operatively connected with the proximal end portion of the cannula assembly 412.

The cannula assembly 412 is essentially constructed as an elongated wall structure providing an exterior periphery suitable to pass through the scope passage and a hollow interior. In the embodiment shown, the elongated wall structure is formed by a central flexible tubular member 416 of a size to receive therein a laser fiber optic probe such as shown in phantom lines in FIG. 25 and designated by the numeral 418. The tubular member 416 is formed of a suitable plastic material such as polyethylene, polypropylene, polyester, polyvinyl chloride, polyimide or the like. For the nephroureteroscopic application shown, there are four spaced helical members in the form of helically wound wire sections 420 fused within the exterior periphery of the central tubular member 416. The helically wound wire sections 420 are preferably made of stainless steel wire with a loop or volute size just sufficient to allow passage of the wire loosely therethrough and a pitch which is several times the wire diameter, as, for example, four.

At the distal end of the cannula assembly 412, the helically wound wire sections 420 extend outwardly of the distal end of the central tubular member 416. The outwardly extending distal end portions of the helically wire sections 420 are preferably changed in pitch to one which is equal to approximately 1½ times the wire diameter. The outwardly extending distal end portions of the helically wound wire sections 420 constitute longitudinally fixed flexure elements 422 forming a part of an annularly expanding and retracting gripping and releasing mechanism, generally indicated at 424, at the distal end of the cannula assembly 412.

The cannula assembly 412 also includes four straight wire sections 426 which are preferably an integral continuation of the stainless steel wire which is used to form the fixed flexure elements 422.

Each wire section 426 has a length in excess of the length of the helically wound wire sections 420. As shown, each wire section 426 is bent at an integral juncture thereof with the distal end of the associated fixed flexure element 422. The integral juncture between the proximal end of each fixed flexure element 422 and the distal end of the remainder of the associated helically would wire section 420 is reinforced by a plastic tape 428 or the like. The taped area constitutes a fixed position of confinement of the cannula assembly 412 from which the fixed flexure elements 422 extend.

In addition, in order to prevent the helical wire which forms each fixed flexure element 22 from expanding or contracting in a longitudinal direction, a plastic tape or painted on body of plastic, indicated at 429, is provided on an annular outer sector of each fixed flexure element 422. The plastic 429 extends thinly over the outer periphery of the loops or volutes of the helical wire and between adjacent loops. The sector configuration of the plastic 429 enables the inner portions of the volutes of the helical wire to expand or contract so that the fixed flexure elements 422 can flex arcuately outwardly as the extracting mechanism 424 is expanded.

The wire used to form the helically wound wire sections 420 can be initially coated with a very thin layer of plastic. The coating makes the fusion with the central tubular member 416 and the tapes 428 and 429 a plastic to plastic fusion and provides the fixed flexure elements 422 with a plastic gripping surface. Alternatively, the inner peripheral portion of the volutes of the helical wire forming each fixed flexure element 422 can be coated with plastic to provide a gripping surface with a better coefficient of friction than stainless steel.

The four wire sections 426 extend within the four helically wound wire sections 420 with the bend being disposed in a flexure position on the longitudinally fixed flexure elements 422 which, as shown, is at the distal free ends of the helically wound wire sections 420. The four wire sections 426 are fixed with respect to the four helically wound wire sections 420 by virtue of being an integral part thereof.

The four wire sections 426 extend within the four helically wound wire sections 420, however, not within the same ones to which they are fixed; but, instead, in adjacent helically wound wire sections 420. Each wire section 426 extends from the bend which connects it adjacent to its helically wound wire member 420 through an adjacent helically wound wire sections 420 and outwardly beyond the proximal end thereof.

The preferred embodiment of the moving assembly 114 shown in FIGS. 25–30 includes a main body, generally indicated at 430, molded of a suitable plastic material or formed of a metal material. The main body 430 is of generally tubular construction and of a size to be conveniently gripped in one hand. The main body 430 is formed of a peripheral wall 432 having an end wall 434 at a rearward end thereof. The forward end of the peripheral wall 432 is exteriorly threaded, as indicated at 436. An elongated slot 438 is formed in the peripheral wall 432 which extends rearwardly from the forward end thereof to a position spaced from the rear wall 434.

Mounted within the interior of the peripheral wall 432 is an insert member, generally indicated at 440. The insert member 440 includes a main body portion 442 which is configured to fit within the forward end of the peripheral wall 432 and the coextensive portion of the slot 438. The insert member 440 also includes a flange-like portion 444 disposed forwardly of the main body portion 442 which is shaped to engage an inner annular portion of the forward edge of the peripheral wall 432.

Extending forwardly from a central portion of the flange-like portion 444 is a forwardly projecting portion 446 which forms a bendable transmission between the rigid main body 430 of the moving assembly 414 and the more flexible cannula assembly 412. The projecting portion 446 terminates forwardly in a scope channel sealing extremity having an exterior periphery 448 which is shaped to cooperate with the movable seal of the scope.

The sealing extremity also includes (1) a central opening 450 sized to receive a proximal end portion of the central tubular member 416 therethrough which extends rearwardly from the main body of the central tubular member 416 fused to the helically wound wire sections 420, and (2) four annularly spaced openings 452 sized to receive therethrough the proximal end portions of the four movable wire sections 426 extending from the terminal proximal ends of the four helically wound wire sections 420 which are disposed in abutting relation to the forward face of the sealing extremity of the projection portion 446.

The short central opening 450 communicates rearwardly with a central opening 454 which extends rearwardly through the insert member 440 including a cylindrical rearward extension portion 456 thereof. The central opening 454 has the shape of a plus with the cross at the center expanded circularly. Stated differently, the opening 454 includes a center portion sized to receive therein the central tubular member 416 and four annularly spaced radiating grooves sized to receive the four movable wires 426 therein.

It will be understood that the position of the sealing surface 448 from the distal end of the cannula 412 is related to the length of the scope so that it will enter the proximal end of the working channel of the scope when the extracting mechanism 424 of the extractor 410 extends from the distal end of the working channel of the scope.

A cap mounting element 458 is centrally apertured to receive therethrough the forward projecting portion 446 so as to be capable of being initially fed forwardly over the proximal end portion of the cannula assembly 412 and then moved rearwardly over the projecting portion 446. The cap mounting element 458 is interiorly threaded to engage with the threads 436 of the peripheral wall 432. When so threadedly engaged, the mounting element 458 serves to secure the insert member 440 and projecting portion 446 to the main body 430.

The cylindrical rearward extension portion 456 of the insert member 440 slidably extends within a central cylindrical opening 460 extending rearwardly from the forward end of a moving member, generally indicated at 462. The rearward end of the cylindrical opening 460 communicates with an opening 464 which has a configuration the same as the opening 454 to receive the central tubular member 416 and four movable wire sections 526 therethrough.

The rear end portion of the moving member 462 is formed with a frusto-conical exterior surface 466 over which the terminal ends of the four movable wire sections 426 are bent. A mounting element 468 in the form of a snap-on cap with an interior frusto-conical surface 470 is snap-fitted (or threadedly engaged) on the end of the moving member 462 to securely fix the movable wire sections 426 thereto. The cap mounting member 468 is centrally apertured to receive therethrough the proximal end portion of the central tubular member 416.

The moving member 462 includes a cylindrical exterior periphery with an upstanding digitally engageable portion 472 which is sized to move through the slot 438 in the main body 430. The digitally engageable portion 472 includes a projection 474 at its forward end for facilitating the digital movement of the moving member 462 in both longitudinal directions with respect to the insert member 440 and the main body 430 between an insertion position, as shown in FIG. 26, and a maximum deployed position disposed in abutting engagement with the main body 442 of the insert member 440.

The moving member 462 is preferably mounted in the main body 430 in assembled relation with the insert member 440 interconnected with the cannula assembly 412 as aforesaid and with the cap mounting element 468 extended over the cannula assembly 412.

It will be noted that the end wall 434 of the main body 430 is centrally apertured to receive the rearward end of the central tubular member 416 extending rearwardly from the centrally apertured cap 468 when the moving member 462 is fully inserted into abutting engagement with the end wall 434.

As shown, the central aperture of the end wall 434 flares outwardly and rearwardly, as indicated at 476, and a centrally apertured cap 478 is provided to fix the proximal end of the central tubular member 416 to the end wall 434 of the main body 430. As shown, an exteriorly threaded annular wall 480 extends rearwardly from the end wall 434 and the cap 478 includes an interiorly threaded skirt 482 capable of being threadedly engaged on the annular wall 480. The cap 478 includes a central annular portion 484 having a surface which mates with the surface 476 to secure the end of the central tubular member 416 therebetween when the cap 478 is screwed into the annular wall 480. In this way, the entire tubular structure of the cannula assembly 412 is fixed to the main body 430 of the moving assembly 414.

In the use of the medical retrieving device 410 in a nephroureteroscopic kidney stone removal procedure, the standard preparatory procedures and standard auxiliary equipment are used, as are the stone-extracting procedures described above in conjunction with the previous extractors.

In situations where the size of the stone is too large to be simply retrieved, it can then be broken up. To accomplish the breaking action, a laser fiber 18 is advanced through the proximal end of the central tubular member 16 until it becomes visible at the distal end adjacent the gripped stone.

A laser is discharged through the fiber 18 to the stone imparting energy enough to break it into smaller fragments. This lithotripsy will usually result in displacing smaller stone fragments outside the confines of the fixed flexure elements 22 with larger fragments which, if not too large, can be retrieved through the ureter with the scope. The smaller fragments can be retrieved by subsequent similar procedures.

It will be understood that the availability of the interior of the central tubular member 16 enables the device 10 to be used with an electrohydraulic lithotripter probe as well as any known laser fiber lithotripter probe in order to accomplish the lithotropsy.

It thus will be seen that the objects of this invention have been fully and effectively accomplished. It will be realized, however, that the foregoing preferred specific embodiment has been shown and described for the purpose of this invention and is subject to change without departure from such principles. Therefore, this invention includes all modifications encompassed within the spirit and scope of the following claims.

What is claimed is:

1. A medical extractor comprising an elongated cannula assembly having a distal end constructed and arranged to be inserted into a patient and a proximal end constructed and arranged to be retained exteriorly of the patient, said cannula assembly having an annularly expanding and retracting gripping and releasing mechanism at the distal end thereof and a moving assembly at the proximal end thereof, said gripping and releasing mechanism including an annular series of longitudinally fixed flexure elements and a corresponding series of longitudinally movable flexure elements, said fixed flexure elements being fixed relatively together in an annular array at a confining fixed position and having a flexure position spaced longitudinally outwardly therefrom, each of said fixed flexure elements being constructed and arranged to flex at the flexure position thereof transversely outwardly and inwardly about the confined fixed position thereof, each of said movable flexure elements having an end fixed with respect to the flexure position of one of said fixed flexure elements and extending therefrom in longitudinally movable and generally transversely confined relation to a receiving portion of an adjacent fixed flexure element the longitudinal outer end of which is adjacent the flexure position thereof, said moving assembly and said cannula assembly being constructed and arranged so that a manual movement of said moving assembly in one direction will effect a movement of said movable flexure elements in an outward direction with respect to the receiving portions associated therewith to extend in an arcuately flexed condition beyond the flexure positions of said fixed flexure elements to cause the latter to flex transversely outwardly and create an expanded condition defined by an annular series of transversely outwardly flexed fixed flexure elements interconnected by an annular series of arcuately flexed portions of said movable flexure elements, said moving assembly and said cannula assembly being constructed and arranged so that a manual movement of said moving assembly in an opposite direction will effect a movement of said movable flexure elements when in said expanded condition in a direction inwardly with respect to the receiving portions associated therewith to cause said expanded condition to progressively retract during which the annular series of transversely outwardly flexed fixed flexure elements are progressively less flexed transversely outwardly and the annular series of arcuately flexed portions of said movable flexure elements have a progressively less arcuate extent.

2. A medical extractor as defined in claim 1 wherein each of said fixed flexure elements is formed of a plastic tubular section, each of said movable flexure elements is formed of a wire section, and the extent of said cannula assembly between said gripping and releasing mechanism and said moving assembly is formed by continuing sections of said plastic tubular sections and first and second continuing sections of said wire sections extending from opposite ends thereof, the first continuing section of each wire section being disposed within and fixed with respect to the plastic tubular section forming one of said fixed flexure elements and the continuing section thereof with the wire section associated therewith extending from the end of the plastic tubular section forming said one fixed flexure element and with the second continuing section thereof extending within and through the plastic tubular section defining as adjacent fixed flexure element and the continuing section thereof.

3. A medical extractor as defined in claim 1 wherein said moving assembly comprises a tubular body constructed and arranged to be gripped in a hand and a moving member mounted within said tubular body for digital reciprocating movement with respect thereto, an end of each continuing section of said plastic tubular sections and an end of each first continuing section of said wire sections being fixed to said tubular body and an end of each second continuing section of said wire sections being fixed to said moving member.

4. A medical extractor as defined in claim 1 wherein each of said fixed flexure elements is formed of a plastic tubular section, each of said movable flexure elements is formed of a wire section, and the extent of said cannula assembly between said gripping and releasing mechanism is formed by an outer tubular member fixed at one end to one end of said plastic tubular sections and first continuing sections of said wire sections, each of said wire sections having a short second continuing section thereof disposed within and fixed with respect to a plastic tubular section forming one of said fixed flexure elements and extending from a free end thereof with the first continuing section thereof extending within and through the plastic tubular section defining an adjacent fixed flexure element and said outer tubular member.

5. A medical extractor as defined in claim 4 wherein said moving assembly comprises a tubular body constructed and arranged to be gripped in a hand and a moving member mounted within said tubular body for digital reciprocating movement with respect thereto, an end of said outer tubular member being fixed to said tubular body and an end of each first continuing section of said wire section being fixed to said moving member.

6. A medical extractor as defined in claim 1 wherein each of said fixed flexure elements is formed of a helically wound wire section, each of said movable flexure elements is formed of a movable wire section and the extent of said cannula assembly between said gripping and releasing mechanism is formed by continuing sections of said helically wound wire sections and continuing sections of said movable wire sections, the continuing sections of said helically wound wire sections being secured together in an annular array corresponding with the annular array of said fixed flexure elements, each of said movable wire sections extending from an end volute of the helically wound wire section forming one of said fixed flexure elements with the continuing section thereof slidably extended within and through the helically wound wire section forming an adjacent fixed flexure element and the continuing section thereof.

7. A medical extractor as defined in claim 6 wherein said moving assembly comprises a tubular body constructed and arranged to be gripped in a hand and a moving member mounted within said tubular body for digital reciprocating movement with respect thereto, an end of each continuing section of said helically wound wire sections being fixed to said tubular body and the end of each continuing section of said movable wire sections being fixed to said moving member.

8. A medical extractor as defined in claim 6 wherein each of said helically wound wire sections includes an end volute secured together to form an annular end loop and each wire section extends tangentially from one of said annular end loops.

9. A medical extractor as defined in claim 8 wherein each annular end loop includes an end integral with an end of the movable wire section extending therefrom.

10. A medical extractor as defined in claim 9 wherein each movable wire section has a circular cross-sectional configuration and the helically wound wire section integral therewith and the continuing section thereof is formed of a wire having a radially flattened cross-sectional configuration of the same cross-sectional area as the circular cross-sectional configuration of the movable wire section.

11. A medical extractor as defined in claim 9 wherein each movable wire section has a circular cross-sectional configuration and the helically wound wire section integral therewith is formed of wire having a circular diameter of a lesser size than said movable wire section.

12. A medical extractor as defined in claim 8 wherein each annular end loop includes a terminal end secured within the annular end loop and the movable wire section extending therefrom is separate and includes an end spot welded to the annular end loop from which the wire section extends.

13. A medical extractor as defined in claim 12 wherein the end of the separate movable wire section extending from each annular end loop is spot welded to the terminal end of the annular end loop.

14. A medical extractor as defined in claim 13 wherein the end of the separate movable wire section extending from each annular end loop is also spot welded to the portion of the annular end loop adjacent the terminal end thereof.

15. A medical extractor as defined in claim 6 wherein the movable wire sections and the continuing sections thereof and the helically wound wire sections and the continuing sections thereof are all formed of stainless steel.

16. A medical extractor as defined in claim 15 wherein the stainless steel is coated with a plastic material, the helically wound wire sections and the continuing sections thereof are formed with adjacent volutes in abutting relation, said volutes being retained in abutting relation by the plastic material coated thereon, the continuing sections of said helically wound wire section being secured in said annular array by the plastic material coated thereon.

17. A medical extractor as defined in claim 16 wherein the continuing sections of said helically wound wire sections are formed with adjacent volutes spaced apart which are secured together in said annular array by fusion with a plastic material of a central elongated member.

18. A medical extractor as defined in claim 17 wherein said central elongated member includes a metallic wire core.

19. A medical extractor as defined in claim 17 wherein said central elongated member is hollow so as to allow the passage of an elongated lithotripter probe therethrough.

20. A medical extractor as defined in claim 17 wherein each of said helically wound wire sections is formed with adjacent volutes other than the annular end loop spaced apart, the spaced apart volutes having a strip of plastic material secured longitudinally along a radially outer portion thereof to provide longitudinal stability.

21. A medical extractor as defined in claim 6 wherein each of said helically wound wire sections is formed with adjacent volutes other than the annular end loop spaced apart, the spaced apart volutes having a strip of plastic material secured longitudinally along a radially outer portion thereof to provide longitudinal stability.

22. A medical extractor as defined in claim 6 wherein the center of the annular array and the center of the moving assembly are formed with a continuous central passage of a size to receive therethrough an elongated lithotriper probe.

23. A method of making a medical extractor comprising
forming a component in the form of a helically wound wire section having (1) a longitudinally stable and transversely flexible end section, (2) a straight wire section extending tangentially from an end loop of said end section, and (3) an adjacent bend in said straight wire section which extends the remaining portion of the straight wire section angularly toward the helically wound wire section,
securing a series of said components together in an assembled relation wherein the helically wound wire sections are disposed in a longitudinally stable and transversely flexible annular array with said end sections disposed in generally coextensive independently flexing relation,
inserting the straight wire section of each component within the end section of an adjacent helically wound wire section, so as to extend outwardly of the opposite end thereof and
connecting a moving assembly to the opposite ends of said helically wound wire sections and the ends of said straight wire sections extending outwardly thereof so that the straight wire sections can be moved with respect to the helically wound wire sections.

24. A method as defined in claim 23 wherein each component is made of stainless steel wire.

25. A method as defined in claim 23 wherein each component is made of stainless steel wire having a plastic coating thereon.

26. A method as defined in claim 25 wherein adjacent volutes of the helically wound wire section of each component are disposed in abutting relation and secured together by the plastic coated thereon.

27. A method as defined in claim 24 wherein adjacent volutes of the helically wound wire section of each component are spaced apart and a plastic strip is adhered along the longitudinal extent of the end section of each component in order to render it longitudinally stable.

28. A method as defined in claim 27 wherein each component is formed from one length of wire of round cross-sectional configuration with the portion of the wire forming the helically wound wire sections being flattened in a radial direction with respect thereto.

29. A method as defined in claim 23 wherein each component is formed from one length of wire.

30. A method as defined in claim 23 wherein the portion of the one length of wire forming the straight wire section of the component has a circular cross-sectional configuration of approximately 8 mils in diameter and the portion of the one length of wire forming the helically wound wire section of the component has a cross-sectional configuration with a radial coil width of approximately 4 mils.

31. A method as defined in claim 30 wherein the helically wound wire section of each component is formed of a first length of wire and the straight wire section of each component is formed of a second length of wire, end portions of said first and second wires being spot welded together.

32. A method as defined in claim 31 wherein said first length of wire has a diameter dimension less than a diameter dimension of said second length of wire.

* * * * *